US006475988B1

(12) United States Patent
Rodgers et al.

(10) Patent No.: US 6,475,988 B1
(45) Date of Patent: Nov. 5, 2002

(54) METHODS TO INCREASE WHITE BLOOD CELL SURVIVAL AFTER CHEMOTHERAPY

(75) Inventors: Kathleen E. Rodgers, Long Beach, CA (US); Gere DiZerega, Pasadena, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 09/307,940

(22) Filed: May 10, 1999

Related U.S. Application Data

(60) Provisional application No. 60/092,633, filed on Jul. 13, 1998, and provisional application No. 60/084,908, filed on May 11, 1998.

(51) Int. Cl.[7] .................. A61K 38/07; A61K 38/08; C07K 5/10; C07K 7/06
(52) U.S. Cl. .............. 514/15; 514/16; 514/17; 514/18; 514/21; 530/327; 530/328; 530/329; 530/330; 930/DIG. 591; 930/DIG. 592
(58) Field of Search .................. 435/172.3, 240.2; 424/85.1, 85.2; 514/2, 12, 14, 18, 21, 16, 15, 17; 530/328, 313, 329, 316, 327, 330; 930/40, DIG. 590, DIG. 591, DIG. 592

(56) References Cited

U.S. PATENT DOCUMENTS

| 5,015,629 A | | 5/1991 | di Zerega .................. 514/16 |
|---|---|---|---|
| 5,527,882 A | * | 6/1996 | Mitchell et al. ............ 530/328 |
| 5,595,973 A | | 1/1997 | Bodgen .................... 514/18 |
| 5,605,931 A | | 2/1997 | Hanson .................... 514/530 |
| 5,629,292 A | | 5/1997 | Rodgers et al. ............. 514/16 |
| 5,693,616 A | | 12/1997 | Krstenansky et al. ......... 514/12 |
| 5,716,935 A | | 2/1998 | Rodgers et al. ............. 514/16 |
| 5,834,432 A | | 11/1998 | Rodgers et al. ............. 514/16 |
| 5,925,343 A | * | 7/1999 | Nash et al. ................ 424/85.1 |
| 5,955,430 A | | 9/1999 | Rodgers et al. ............. 514/16 |
| 6,239,109 B1 | * | 5/2001 | Rodgers et al. ............. 514/16 |

FOREIGN PATENT DOCUMENTS

| JP | 07215889 A | * | 8/1995 |
|---|---|---|---|
| WO | WO 95/08337 | | 3/1995 |
| WO | WO 95/08565 | | 3/1995 |
| WO | WO 96/14858 | | 5/1996 |
| WO | WO 9614858 A1 | * | 5/1996 |
| WO | WO 96/15795 | | 5/1996 |
| WO | WO 96/39164 | | 12/1996 |
| WO | WO 96/40090 | | 12/1996 |
| WO | WO 97/27867 | | 8/1997 |
| WO | WO 97/34627 | | 9/1997 |
| WO | WO 98/26795 | | 6/1998 |
| WO | WO 98/32457 | | 7/1998 |
| WO | WO 98/33813 | | 8/1998 |

OTHER PUBLICATIONS

Elizondo, Jr. et al. Effect of angiotensin II on immunotoxin ... Cancer Chemother. Pharmacol. vol. 39, pp. 113–121, 1996.*

Gerhartz et al., Intervention Treatment of Established Neutropenia with Human Recombinant Granulocyte–Macrophage–Colony–Stimulating Factor (rhGM–CSF) in Patients undergoing Cancer Chemotherapy, Leukemia Research (1993 Feb.) 17(2): 175–85.*

(List continued on next page.)

Primary Examiner—Jeffrey E. Russel
(74) Attorney, Agent, or Firm—McDonnell, Boehnen Hulbert & Berghoff; David S. Harper

(57) ABSTRACT

The present invention provides improved methods, kits, and pharmaceutical compositions for increasing white blood cell survival following chemotherapy, and mobilizing hematopoietic progenitor cells from bone marrow into peripheral blood, comprising the administration of an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists.

18 Claims, 30 Drawing Sheets

Blood, day 7.

OTHER PUBLICATIONS

Lehninger et al., Biochemistry, 2d ed. (1993) pp. 154–155.*

Li et al., Augmentation of tumor delivery of macromolecular drugs with reduced bone marrow delivery by elevating blood pressure, Br. J. Cancer (1993) 67:975–980.*

Tewksbury et al., The Amino Terminal Acid Sequence of Human Angiotensin, Biochemical and Biophysical Research Comm. (1981) 99(4): 1311–1315.*

Mrug, M., et al., (1997) *J. Clin. Invest.*, 100, pp. 2310–2314.

Bell, et al., (1990), *American Journal of Pathology*, "Rapid Communication: Influence of the Angiotensin System on Endothelial and Smooth Muscle Cell Migration", 137(1): pp. 7–12.

Berk, et al., (1989), *Hypertension*, "Angiotensin II–Stimulated Protein Synthesis in Cultured Vascular Smooth Muscle Cells", 13: pp. 305–314.

Bryson, et al., (1992), *Eur. J. of Pharm.*, "Induction of the Angiotensin $AT_2$ Receptor Subtype Expression by Differentiation of the Neuroblastoma X Glioma Hybrid, NG–108–15.", 225: pp. 119–127.

Elizondo, Jr., et al., (1996), *Cancer Chemother. Pharmacol.*, "Effect of Angiotensin II on Immunotoxin Uptake in Tumor and Normal Tissue", 39: pp. 113–121.

Catalioto, et al., (1994), *Eur. J. of Pharmacology.*, "Angiotensins Induce the Release of Prostacyclin from Rabbit Vas Deferens: Evidence for Receptor Heterogeneity", 256: pp. 93–97.

Clouston, et al., (1988), *Genomics*, "Molecular Cloning of the Mouse Angiotensinogen Gene", 2: pp. 240–248.

Dworkin, et al., (1997), *British J. of Cancer*, "Effect of Continuous Regional Vasoactive Agent Infusion on Liver Metastasis Blood Flow", 76(9): pp. 1205–1210.

Dzau, et al., (1989), *J. Mol. Cell. Cardiol*, 21:S7 (Supplement III).

Edwards, et al., (1993), *J. of Pharmacology and Exp. Ther.*, "Angiotensin II Inhibits Glomerular Adenylate Cyclase Via the Angiotensin II Receptor Subtype 1 ($AT_1$)", 266(2): pp. 506–510.

Fernandez, et al., (1985), *J. Lab. Clin. Med.*, "Neovascularization Produced by Angiotensin II", 105(2): pp. 141–145.

Jaiswal, et al., (1992), *Hypertension*, "Stimulation of Endothelial Cell Prostaglandin Production by Angiotensin Peptides",19(Supp. II): pp. II–49—II–55.

Jaiswal, et al., (1993), *J. Pharmacol. Exper. Ther*, "Differntial Regulation of Prostaglandin Synthesis by Angiotensin Peptides in Porcine Aortic Smooth Muscle Cells: Subtypes of Angiotensin Receptors Involved[1]", 265(2): pp. 664–673.

Jaiswal, et al., (1991), *Hypertension*, "Subtype 2 Angiotensin Receptors Mediate Prostaglandin Synthesis in Human Astrocytes", 17: pp. 1115–1120.

Janiak, et al., (1992), *Hypertension*, "Role of Angiotensin Subtype 2 Receptor in Neointima Formation After Vascular Injury", 20: pp. 737–745.

Jimenez, et al., (1992), *Cancer Research*, "Protection form 1–β–D–Arabinofuranosylcytosine–Induced Alopecia by Epedermal Growth Factor and Bibroblast Growth Factor and Bibroblast Growth Factor in the Rat Model", 52: pp. 413–415.

Kageyama, et al., (1984) *Biochemistry*, "Primary Structure of Human Preangiotensinogen Deduced from the Cloned cDNA Sequence", 23: pp. 3603–3609.

Kauffman, et al., (1991), *Life Sci.*, "Losartan, A Nonpeptide Angiotensin II (Ang II) Receptor Antagonist, Inhibits Neointima Formation Following Balloon Injury To Rat Carotid Arties", 49: pp. PL–223—PL–228.

Kawahara, et al., (1988), *BBRC*, "Angiotensin II Induces Expression of the C–FOS Gene Through Protein Kinase C Activation and Calcium Ion Mobilization in Cultured Vascular Smooth Muscle Cells[1]", 150(1): pp. 52–59.

Kimura, et al., (1992), *BBRC*, "Changes in Skin Angiotensin II Receptors in Rats During Wound Healing", 187(2): pp. 1083–1090.

Kuroiwa, et al., (1995), *Cancer Chemother. Pharmacol.*, "Phase II Study of a New Combined Primary Chemotherapy Regimen, Intravenous Methotrexate and Vincristine and Intraarterial Adriamycin and Cisplatin, for Locally Advanced Urinary Bladder Cancer: Preliminary Results", 35: pp. 357–363.

Le Noble, et al., (1991), *Eur. J. of Pharmacology*, "Angiotensin II Stimulates Angiogenesis in the Chorio–Allantoic Membrane of the Chick Embryo", 195: pp. 305–306.

Li, et al., (1993), *Br. J. Cancer*, "Augmentation of Tumour Delivery of Macromolecular Drugs with Reduced Bone Marrow Delivery by Elevating Blood Pressure", 67: pp. 975–980.

Morita, et al., (1992), *Am J. Clin. Oncol.*, "Intraarterial Infusion Chemotherapy with [Sar [1], Ile[8]] Angiotensin II for Bladder Cancer", 15(3): pp. 188–193.

Mutoh, et al., (1992), *Urol. Int.*, "Local Control of Prostate Cancer by Intraarterial Infusion Chemotherapy Facilitated by the Use of Angiotensin II", 48: pp. 175–180.

Naftilan, et al., (1989), *J. Clin. Invest.*, "Induction of Platelet–Derived Growth Factor A–Chain and c–myc Gene Expressions by Angiotensin II in Cultured Rat Vascular Smooth Muscle Cells", 83: pp. 1419–1423.

Nakahara, et al., (1992), *BBRC*, "Identification of Three Types of PDGF–A Chain Gene Transcripts in Rabbit Vascular Smooth Muscle and Their Regulated Expression During and by Angiotensin II", 184(2): pp. 811–818.

Ohigashi, et al., (1996), *Gastroenterology*, "A New Method of Intra–Arterial Regional Chemotherapy with More Selective Drug Delivery for Locally Advanced Pancreatic Cancer", 43: pp. 338–345.

Ohkubo, et al., (1983), *Proc. Natl. Acad. Sci. USA*, "Cloning and Sequence Analysis of cDNA for Rat Angiotensinogen", 80: pp. 2196–2200.

Pfeilschifter, et al., (1992), *Eur. J. Pharmacol.*, "Angiotensin II Stimulation of Phospholipase D in Rat Renal Mesangial Cells is Mediated by the $AT_1$ Receptor Subtype", 225: pp. 57–62.

Pörtsi, et al., (1994), *Br. J. Pharmacol.*, "Release of Nitric Oxide by Angiotensin–(1–7) from Porcine Coronary Endothelium: Implication s for a Novel Angiotensin Receptor", 111: pp. 652–654.

Prescott, et al.,(1991), *Am. J. Pathol.*, "Rapid Communication: Angiotensin–converting Enzyme Inhibitor Versus Angiotensin II, $AT_1$ Receptor Antagonist", 139(6): pp. 1291–1296.

Regoli, et al., (1974), *Pharmacological Reviews*, "Pharmacology of Angiotensin", 26(2): pp. 69–123.

Sato, et al., (1995), *World J. Surg.*, "Angiotensin II (AII) Induced Hypertension Chemotherapy (IHC) for Unresectable Gastric Cancer: With Reference to Resection after Down Staging", 19: pp. 836–842.

Speth, et al., (1990), *BBRC,* "Discrimination of Two Angiotensin II Receptor Subtypes with a Selective Agonist Analogue of Angiotensin II, p–Aminophenylalanine$^6$ Angiotensin II", 169(3): pp. 997–1006.

Stouffer, et al., (1992), *Circ. Res.,* "Angiotensin II–Induced Mitogenesis of Spontaneoulsy Hypertensive Rat–Derived Cultured Smooth Muscle Cells Is Dependent on Autocrine Production of Transforming Growth Factor–β", 70: pp. 820–828.

Taniguchi, et al., (1996), *J. Nuclear Medicine,* "Angiotensin–II–Induced Hypertension Chemotherapy: Evanluation of Hepatic Blood Flow With Oxygen–15 PET", 37(9): pp. 1522–1523.

Taubman, et al., (1989), *J. Biol. Chem.,* "Angiotensin II Induces c–fos mRNA in Aortic Smooth Muscle", 264: pp. 526–530.

Taubiana, et al., (1993), *Radiotherapy and Oncology,* "Ways of Miimising Hematopoietic Damage Induced by Radiation and Cytostatic Drugs–The Possible Role of Inhibitors", 29: pp. 1–17.

Viswanathan, et al., (1992), *Peptides* "Expression of Angiotensin II AT$_3$ Receptors in the Rat Skin During Experimental Wound Healing", pp. 783–786.

Wolf, et al., (1992), *Am. J. Pathol.,* "Angiotensin II Stimulates the Proliferation and Biosynthesis of Type I Collagen in Cultured Murine Mesangial Cells", 140(1): pp. 95–107.

\* cited by examiner

US 6,475,988 B1

METHODS TO INCREASE WHITE BLOOD CELL SURVIVAL AFTER CHEMOTHERAPY

CROSS REFERENCE

This application claims priority to U.S. Provisional Application No. 60/084,908 filed May 11, 1998 and No. 60/092,633 filed Jul. 13, 1998.

FIELD OF THE INVENTION

The present invention relates to methods, kits, and pharmaceutical compositions for increasing white blood cell survival following chemotherapy and for mobilizing hematopoietic cell precursors from the bone marrow to the peripheral blood.

BACKGROUND OF THE INVENTION

People diagnosed as having cancer are frequently treated with single or multiple cytotoxic chemotherapeutic agents (cytotoxic agents) to kill cancer cells at the primary tumor site or at distant sites to where cancer has metastasized. (U.S. Pat. No. 5,605,931 incorporated by reference herein in its entirety.) Chemotherapy treatment is given either in a single or in several large doses or, more commonly, it is given in small doses 1 to 4 times a day over variable times of weeks to months. There are many cytotoxic agents used to treat cancer, and their mechanisms of action are generally poorly understood.

Irrespective of the mechanism, useful chemotherapeutic agents are known to injure and kill cells of both tumors and normal tissues. The successful use of chemotherapeutic agents to treat cancer depends upon the differential killing effect of the agent on cancer cells compared to its side effects on critical normal tissues. Among these effects are the killing of hematopouetic blood forming cells, and the killing and suppression of the white blood cells, which can lead to infection. Acute and chronic bone marrow toxicities are also major limiting factors in the treatment of cancer. They are both related to a decrease in the number of hemopoietic cells (e.g., pluripotent stem cells and other progenitor cells) caused by both a lethal effect of cytotoxic agents or radiation on these cells and by differentiation of stem cells provoked by a feed-back mechanism induced by the depletion of more mature marrow compartments. (U.S. Pat. No. 5,595,973 incorporated by reference herein in its entirety.) Stimulators and inhibitors of bone marrow kinetics play a prominent role in the induction of damage and recovery patterns (Tubiana, M., et al., Radiotherapy and Oncology 29:1, 1993).

Prevention or protection from the side effects of chemotherapy would be a great benefit to cancer patients. The many previous efforts to reduce these side effects have been largely unsuccessful. For life-threatening side effects, efforts have concentrated on altering the dose and schedules of the chemotherapeutic agent to reduce the side effects. Other options are becoming available, such as the use of colony stimulating factor (CSF), granulocyte-macrophage-CSF (GM-CSF) or epidermal growth factor (EGF) to increase the number of normal cells in various tissues before the start of chemotherapy (See Jimenez and Yunis, Cancer Research 52:413–415; 1992). The mechanisms of protection by these factors, while not fully understood, are most likely associated with an increase in the number of normal critical target cells before treatment with cytotoxic agents, and not with increased survival of cells following chemotherapy.

Acute myelosuppression as a consequence of cytotoxic chemotherapy is well recognized as a dose-limiting factor in cancer treatment. (U.S. Pat. No. 5,595,973) Although other normal tissues may be adversely affected, bone marrow is particularly sensitive to the proliferation-specific treatment such as chemotherapy or radiotherapy. For some cancer patients, hematopoietic toxicity frequently limits the opportunity for chemotherapy dose escalation. Repeated or high dose cycles of chemotherapy may be responsible for severe stem cell depletion leading to important long-term hematopoietic sequelea and marrow exhaustion.

Despite advances in the field of chemotherapy, prior art methods have proven to be of limited utility in minimizing chemotherapy-induced hematopoietic stem cell and white blood cell depletion. Thus, there is a need for improved therapeutic methods and pharmaceutical compositions for increasing white blood cells survival following chemotherapeutic treatments, as well as for decreasing the adverse effects of chemotherapy on the bone marrow.

SUMMARY OF THE INVENTION

In one aspect, the present invention provides methods and kits for increasing white blood cell survival following chemotherapy comprising the administration of angiotensinogen, angiotensin I (AI), AI analogues, AI fragments and analogues thereof, angiotensin II (AII), AII analogues, AII fragments or analogues thereof or AII $AT_2$ type 2 receptor agonists.

In another aspect, the present invention provides methods and kits for mobilizing hematopoietic progenitor cells from bone marrow into peripheral blood comprising the administration of angiotensinogen, angiotensin I (AI), AI analogues, AI fragments and analogues thereof, angiotensin II (AII), AII analogues, AII fragments or analogues thereof or AII $AT_2$ type 2 receptor agonists.

In a further aspect, the present invention provides compositions useful for increasing white blood cell survival and mobilizing hematopoietic progenitor cells from bone marrow into peripheral blood following chemotherapy comprising the administration of angiotensinogen, angiotensin I (AI), AI analogues, AI fragments and analogues thereof, angiotensin II (AII), AII analogues, AII fragments or analogues thereof or AII $AT_2$ type 2 receptor agonists.

These aspects and other aspects of the invention become apparent in light of the following detailed description.

DETAILED DESCRIPTION OF THE PREFERRED EMBODIMENTS

Figure 1:
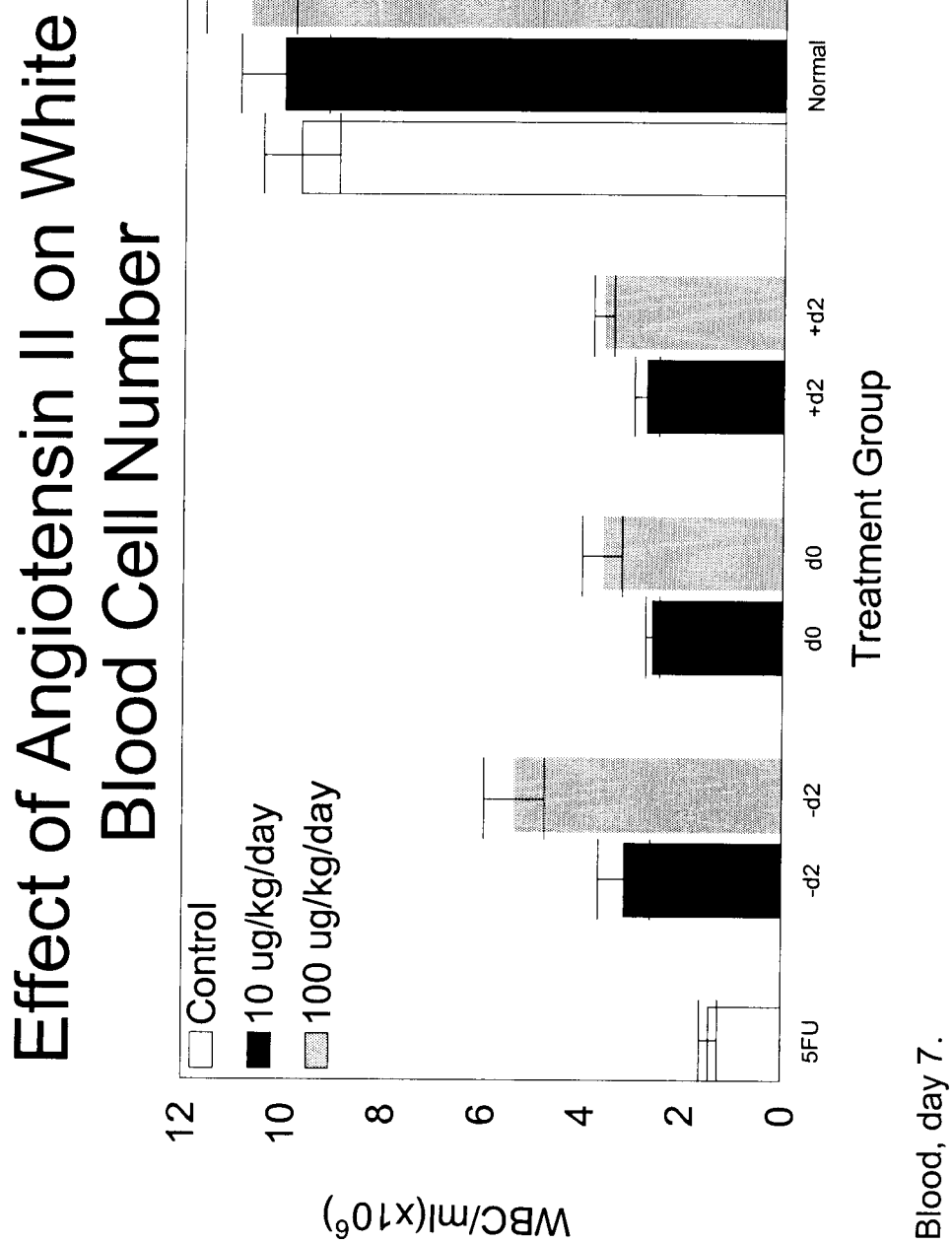
FIG. 1 is a graph showing the effect of AII treatment on white blood cell number in the blood 7 days after 5FU treatment.

All references patents and patent applications are hereby incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As defined herein the phrase "white blood cells" refers to both undifferentiated hematopoietic stem cells, to committed hematopoietic progenitor cells, and to all white blood cells including, but not limited to megakaryocytes, platelets, monocytes, neutrophils, and lymphocytes.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (Clouston et al., *Genomics* 2:240–248 (1988); Kageyama et al, *Biochemistry* 23:3603–3609; Ohkubo et al., *Proc. Natl. Acad. Sci.* 80:2196–2200 (1983); each reference hereby incorporated in its entirety). The substance so formed is a decapeptide called angiotensin I (AI) which is converted to AII by the angiotensin converting enzyme (ACE) which removes the C-terminal His-Leu residues from AI [SEQ ID NO: 37]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264:526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195:305–6 (1991). Additionally, AII and angiotensin III analogs and fragments thereof have been shown to be effective in tissue repair. (U.S. Pat. No. 5,629,292; International Application No. WO 95/08565; International Application WO 95/08337; International Application No. WO 96/39164; all references hereby incorporated in their entirety.) Angiotensin II and its sarcosine analogue have also been used in combination with cytotoxic drugs to induce hypertension in humans and experimental animals undergoing intra-arterial and intraperitoneal chemotherapy. (Taniguchi et al., J. Nuclear Medicine 37:1522–1523 (1996); Morita et al., Am. J. Clin. Oncol. 15:188–193 (1992); Ohigashi et al., Hepato-Gastroenterology 43:338–345 (1996); Cancer Chemother. Pharmacol. 39:113–121 (1996); Kuroiwa et al., Cancer Chemother. Pharmacol. 35:357–363 (1995); Li et al., Br. J. Cancer 67:975–980 (1993); Dworkin et al., Br. J. Cancer 76:1205–1210 (1997); Sato et al., World J. Surg. 19:836–842 (1995); Mutoh et al., Urol. Int. 48:175–180 (1992). In each of these cases, the use of angiotensin II was intended to selectively increase blood flow to the tumor vasculature relative to normal vasculature, thereby increasing the delivery of cytotoxic agent to the tumor. None of these studies demonstrated or suggested that the use of angiotensin II or its sarcosine analogue would be effective in increasing white blood cell survival following chemotherapy.

Based on all of the above, it would be unexpected that the use of angiotensinogen, angiotensin I (AI), AI analogues, AI fragments and analogues thereof, AII, AII analogues, AII fragments or analogues thereof or AII $AT_2$ type 2 receptor agonists would be effective in increasing white blood cell survival following chemotherapy, or for mobilizing hematopoietic progenitor cells from bone marrow into peripheral blood.

A peptide agonist selective for the AT2 receptor (AII has 100 times higher affinity for AT2 than AT1) has been identified. This peptide is p-aminophenylalanine 6-AII ["(p-NH2-Phe)6-AII)"], Asp-Arg-Val-Tyr-Ile-Xaa-Pro-Phe [SEQ ID NO.36] wherein Xaa is p-$NH_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffinan, et al., *Life Sci.* 49:223–228 (1991); Viswanathan, et al., *Peptides* 13:783–786 (1992); Kimura, et al., *BBRC* 187:1083–1090 (1992).

Many studies have focused upon AII(1–7) (AII residues 1–7) or other fragments of AII to evaluate their activity. AII(1–7) elicits some, but not the fall range of effects elicited by AII. Pfeilschifter, et al., *Eur. J. Pharmacol.* 225:57–62 (1992); Jaiswal, et al., *Hypertension* 19(Supp. II):II-49–II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994).

As hereinafter defined, a preferred class of AT2 agonists for use in accordance with the present invention comprises angiotensinogen, angiotensin I (AI), AI analogues, AI fragments and analogues thereof, AII, AII analogues, AII fragments or analogues thereof or AII $AT_2$ type 2 receptor agonists having p-NH-Phe in a position corresponding to a position 6 of AII. In addition to peptide agents, various nonpeptidic agents (e.g., peptidomimetics) having the requisite AT2 agonist activity are further contemplated for use in accordance with the present invention.

The active AII analogues, fragments of AII and analogues thereof of particular interest in accordance with the present invention comprise a sequence consisting of at least three contiguous amino acids of groups $R^1$–$R^8$ in the sequence of general formula I

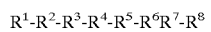

in which $R^1$ and $R^2$ together form a group of formula

wherein X is H or a one to three peptide group,
$R^A$ is suitably selected from Asp, Glu, Asn, Acpc (1-aminocyclopentane carboxylic acid), Ala, $Me^2Gly$, Pro, Bet, Glu($NH_2$), Gly, Asp($NH_2$) and Suc,
$R^B$ is suitably selected from Arg, Lys, Ala, Orn, Ser(Ac), Sar, D-Arg and D-Lys;
$R^3$ is selected from the group consisting of Val, Ala, Leu, Lys, norLeu, Ile, Gly, Pro, Aib, Acpc and Tyr;
$R^4$ is selected from the group consisting of Tyr, Tyr($PO_3$)$_2$, Thr, Ser, Ala, homoSer and azaTyr;
$R^5$ is selected from the group consisting of Ile, Ala, Leu, norLeu, Val and Gly;
$R^6$ is His, Arg or 6-$NH_2$-Phe;
$R^7$ is Pro or Ala; and
$R^8$ is selected from the group consisting of Phe, Phe(Br), Ile and Tyr, excluding sequences including $R^4$ as a terminal Tyr group.

Compounds falling within the category of AT2 agonists useful in the practice of the 15 invention include the AII analogues set forth above subject to the restriction that $R^6$ is p-NH2-Phe. In a further preferred embodiment of all of the aspects of the invention, the sequence is selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, SEQ ID NO:41, and SEQ ID NO:42.

Particularly preferred combinations for $R^A$ and $R^B$ are Asp-Arg, Asp-Lys, Glu-Arg and Glu-Lys.

Particularly preferred embodiments of this class include the following: AII, AIII or AII(2–8), Arg-Val-Tyr-Ile-His-Pro-Phe [SEQ ID NO:2]; AII(3–8), also known as des1-AII or AIV, Val-Tyr-Ile-His-Pro-Phe [SEQ ID NO:3]; AII(1–7), Asp-Arg-Val-Tyr-Ile-His-Pro {SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7]; AII(1–6), Asp-Arg-Val-Tyr-Ile-His [SEQ ID NO:8]; AII(1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6–8), His-Pro-Phe [SEQ ID NO:14] and AII (4–8), Tyr-Ile-His-Pro-Phe [SEQ ID NO:15] were also tested and found not to be effective.

In a particularly preferred embodiment, the active compounds of the present invention are selected from those comprising the following general formula:

Asp-Arg-R1-R2-Ile-His-Pro-R3 (SEQ ID NO:42), wherein

R1 is selected from the group consisting of Val, Pro, Lys, norLeu, and Leu;

R2 is selected from the group consisting of Ala, Tyr, and Tyr($PO_3$)$_2$;

R3 is Phe or is absent.

In a most particularly preferred embodiment, the active compound is selected from the group consisting of SEQ ID NO:1, SEQ ID NO:4, SEQ ID NO:31, SEQ ID NO:32, SEQ ID NO:33, SEQ ID NO:38, SEQ ID NO:39, SEQ ID NO:40, and SEQ ID NO:41.

Another class of compounds of particular interest in accordance with the present invention are those of the general formula II $R^2$-$R^3$-$R^4$-$R^5$-$R^6$$R^7$-$R^8$ in which $R^2$ is selected from the group consisting of H, Arg, Lys, Ala, Orn, Ser(Ac), Sar, D-Arg and D-Lys;

$R^3$ is selected from the group consisting of Val, Ala, Leu, norLeu, Lys, Ile, Gly, Pro, Aib, Acpc and Tyr;

$R^4$ is selected from the group consisting of Tyr, Tyr($PO_3$)$_2$, Thr, Ser, Ala homoSer and azaTyr;

$R^5$ is selected from the group consisting of Ile, Ala, Leu, norLeu, Val and Gly;

$R^6$ is His, Arg or 6-$NH_2$-Phe;

$R^7$ is Pro or Ala; and $R^8$ is selected from the group consisting of Phe, Phe(Br), Ile and Tyr.

A particularly preferred subclass of the compounds of general formula II has the formula $R^2$-$R^3$-Tyr-$R^5$-His-Pro-Phe [SEQ ID NO:16]

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO: 17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me$^2$Gly | N,N-dimethylglycyl |
| Bet | 1-carboxy-N,N,N-trimethylmethanaminium hydroxide inner salt betaine |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., *Pharmacological Reviews* 26:69 (1974)). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr. Lys has also been found to be effective at position $R^3$.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr ($PO_3$)$_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). Ala has also been found to be effective at position $R^4$.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the angiotensinogen, AI, AI analogues, AI fragments and analogues thereof, AII analogues, fragments and analogues of fragments of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr($PO_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be produced by any standard method, including but not limited to recombinant DNA technology and conventional synthetic methods including, but not limited to, those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

In one aspect, the present invention provides methods and kits for increasing white blood cell survival following chemotherapy comprising the administration of angiotensinogen, angiotensin I (AI), AI analogues, AI fragments and analogues thereof, angiotensin II (AII), AII analogues, AII fragments or analogues thereof or AII $AT_2$ type 2 receptor agonists (hereinafter referred to as "active agents").

In another aspect, the present invention provides methods and kits for mobilizing hematopoietic progenitor cells from bone marrow into peripheral blood comprising the administration of the active agents of the invention to a patient in need of such treatment. This aspect of the invention can also be used to treat a patient in need of chemotherapy.

The methods of the invention are appropriate for use with chemotherapy using any cytotoxic agent, including, but not limited to, cyclophosphamide, taxol, 5-fluorouracil, adriamycin, cisplatinum, methotrexate, cytosine arabinoside, mitomycin C, prednisone, vindesine, carbaplatinum, and vincristine. The cytotoxic agent can also be an antiviral compound which is capable of destroying proliferating cells. For a general discussion of cytotoxic agents used in chemotherapy, see Sathe, M. et al., Cancer Chemotherapeutic Agents: Handbook of Clinical Data (1978), hereby incorporated by reference.

The methods of the invention are also particularly suitable for those patients in need of repeated or high doses of chemotherapy. For some cancer patients, hematopoietic toxicity frequently limits the opportunity for chemotherapy dose escalation. Repeated or high dose cycles of chemotherapy may be responsible for severe stem cell depletion leading to important long-term hematopoietic sequelea and marrow exhaustion. The methods of the present invention provide for improved mortality and blood cell count when used in conjunction with chemotherapy.

The active agents may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally.

The active agents may be made up in a solid form (including granules, powders or suppositories) or in a liquid form (e.g., solutions, suspensions, or emulsions). The compounds of the invention may be applied in a variety of solutions. Suitable solutions for use in accordance with the invention are sterile, dissolve sufficient amounts of the peptide, and are not harmful for the proposed application. In this regard, the compounds of the present invention are very stable but are hydrolyzed by strong acids and bases. The compounds of the present invention are soluble in organic solvents and in aqueous solutions at pH 5–8.

The active agents may be subjected to conventional pharmaceutical operations such as sterilization and/or may contain conventional adjuvants, such as preservatives, stabilizers, wetting agents, emulsifiers, buffers etc.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen for increasing white blood cell survival following chemotherapy and mobilizing hematopoietic progenitor cells from bone marrow into peripheral blood with the active agents is based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods. Dosage levels of the order of between 0.1 ng/kg and 10 mg/kg body weight of the active agents per body weight are useful for all methods of use disclosed herein.

The treatment regime will also vary depending on the disease being treated, based on a variety of factors, including the type of injury, the age, weight, sex, medical condition of the individual, the severity of the condition, the route of administration, and the particular compound employed. For example, the active agents are administered to an oncology patient for up to 30 days prior to a course of chemotherapy and for up to 60 days post-chemotherapy. The therapy is administered for 1 to 6 times per day at dosages as described above.

In all of these embodiments, the compounds of the invention can be administered either prior to, simultaneously with, or subsequent to chemotherapeutic exposure.

In a preferred embodiment, the active agent is administered subcutaneously. A suitable subcutaneous dose of the active agent is preferably between about 0.1 ng/kg and about 10 mg/kg administered twice daily for a time sufficient to increase white blood cell survival after chemotherapy treatment or to mobilize hematopoietic progenitor cells from bone marrow into peripheral blood. In a more preferred embodiment, the concentration of active agent is between about 100 ng/kg body weight and about 10.0 mg/kg body weight. In a most preferred embodiment, the concentration of active agent is between about 10 µg/kg body weight and about 10.0 mg/kg body weight. This dosage regimen maximizes the therapeutic benefits of the subject invention while minimizing the amount of agonist needed. Such an application minimizes costs as well as possible deleterious side effects.

For subcutaneous administration, the active ingredient may comprise from 0.0001% to 10% w/w, e.g., from 1% to 2% by weight of the formulation, although it may comprise as much as 10% w/w, but preferably not more than 5% w/w, and more preferably from 0.1% to 1% of the formulation.

In another preferred embodiment of the present invention, the active agent is administered topically. Suitable topical doses and active ingredient concentration in the formulation are as described for subcutaneous administration.

In a most preferred embodiment, subcutaneous administration of between about 1 to 1000 µg/kg/day of the active agents is initiated at between one week before to one week after administration of a chemotherapeutic agent.

In another preferred embodiment of the invention, a subject undergoes repeated cycles of treatment according to the method of this invention. Preferably, a subsequent treatment cycle commences only after the administration of the compounds of the invention have been terminated and the subject's blood cell counts (e.g., white blood cell count) have returned to a therapeutically acceptable level (as determined by the attending veterinarian or physician), permitting the repeated chemotherapy.

In a further aspect, the present invention provides kits for increasing white blood cell survival following chemotherapy and/or mobilizing hematopoietic progenitor cells from bone marrow into peripheral blood, wherein the kits comprise an effective amount of the active agents for increasing white blood cell survival following chemotherapy or for mobilizing hematopoietic progenitor cells from bone marrow into peripheral blood, and instructions for using the amount effective of active agent as a therapeutic. In a preferred embodiment, the kit further comprises a pharmaceutically acceptable carrier, such as those adjuvants described above. In another preferred embodiment, the kit further comprises a means for delivery of the active agent to a patient. Such devices include, but are not limited to syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery may either contain the effective amount of the active agents, or may be separate from the compounds, which are then applied to the means for delivery at the time of use.

In another aspect of the invention, the method comprises pharmaceutical compositions for use in increasing white blood cell survival and/or mobilizing hematopoietic progenitor cells from bone marrow into peripheral blood following chemotherapy, comprising the active agents of the invention, an amount effective for decreasing the growth or neoplastic cells of an anti-neoplastic agent, and a pharmaceutically acceptable carrier. According to this aspect of the invention, any cytotoxic agent can be included in the pharmaceutical composition, including, but not limited to, cyclophosphamide, taxol, 5-fluorouracil, adriamycin, cisplatinum, methotrexate, cytosine arabinoside, mitomycin C, prednisone, vindesine, carbaplatinum, and vincristine. The cytotoxic agent can also be an antiviral compound that is capable of destroying proliferating cells. For a general discussion of cytotoxic agents used in chemotherapy, see Sathe, M. et al., Cancer Chemotherapeutic Agents: Handbook of Clinical Data (1978), hereby incorporated by reference.

The methods, kits, and pharmaceutical compositions of the present invention, by increasing white blood cell survival following chemotherapy and mobilizing hematopoietic progenitor cells from bone marrow into peripheral blood, significantly enhance the utility of presently available treatments for clinical chemotherapeutic treatments.

The present invention may be better understood with reference to the accompanying example that is intended for purposes of illustration only and should not be construed to limit the scope of the invention, as defined by the claims appended hereto.

EXAMPLE 1

Effect of AII on White Blood Cell Mobilization and Recovery After 5 Fluorouracil Treatment This study was designed to test the effect of AII on the recovery of white blood cells in lymphoid organs and on the level of granulocyte macrophage precursors (CFU-GM) in the blood (ie: mobilization), spleen (mobilization), and bone marrow (recovery) after intravenous administration of 5-fluorouracil (5FU).

Figure 2:
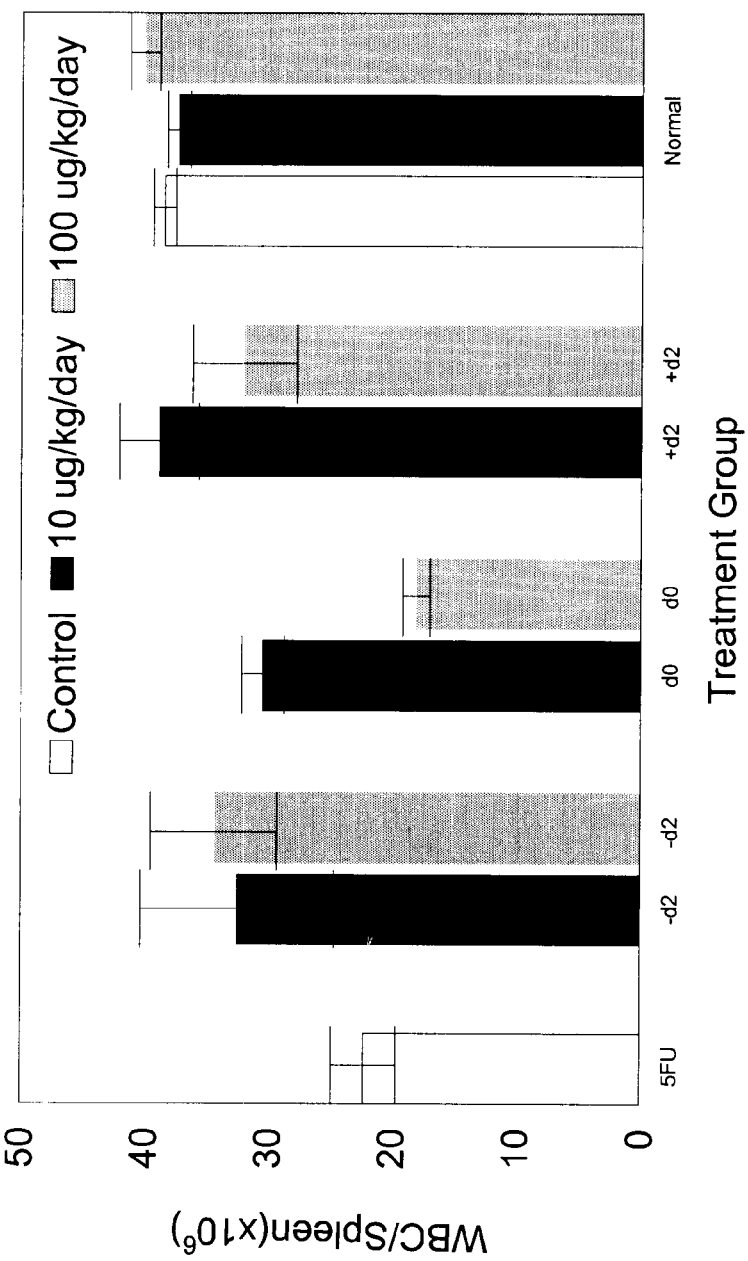
FIG. 2 is a graph showing the effect of AII treatment on white blood cell number in the spleen 7 days after 5FU treatment.
Figure 3:
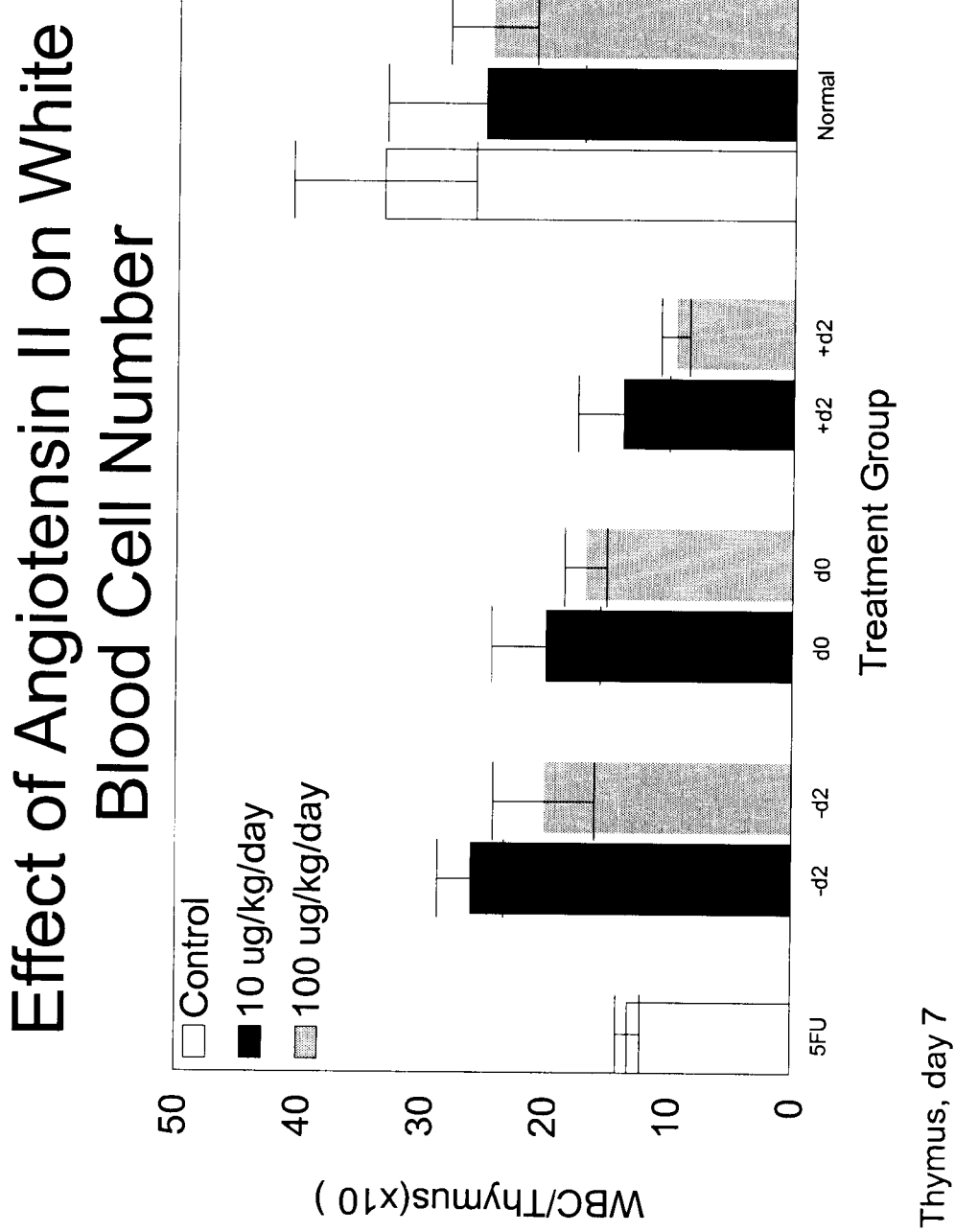
FIG. 3 is a graph showing the effect of AII treatment on white blood cell number in the thymus 7 days after 5FU treatment.
Figure 4:
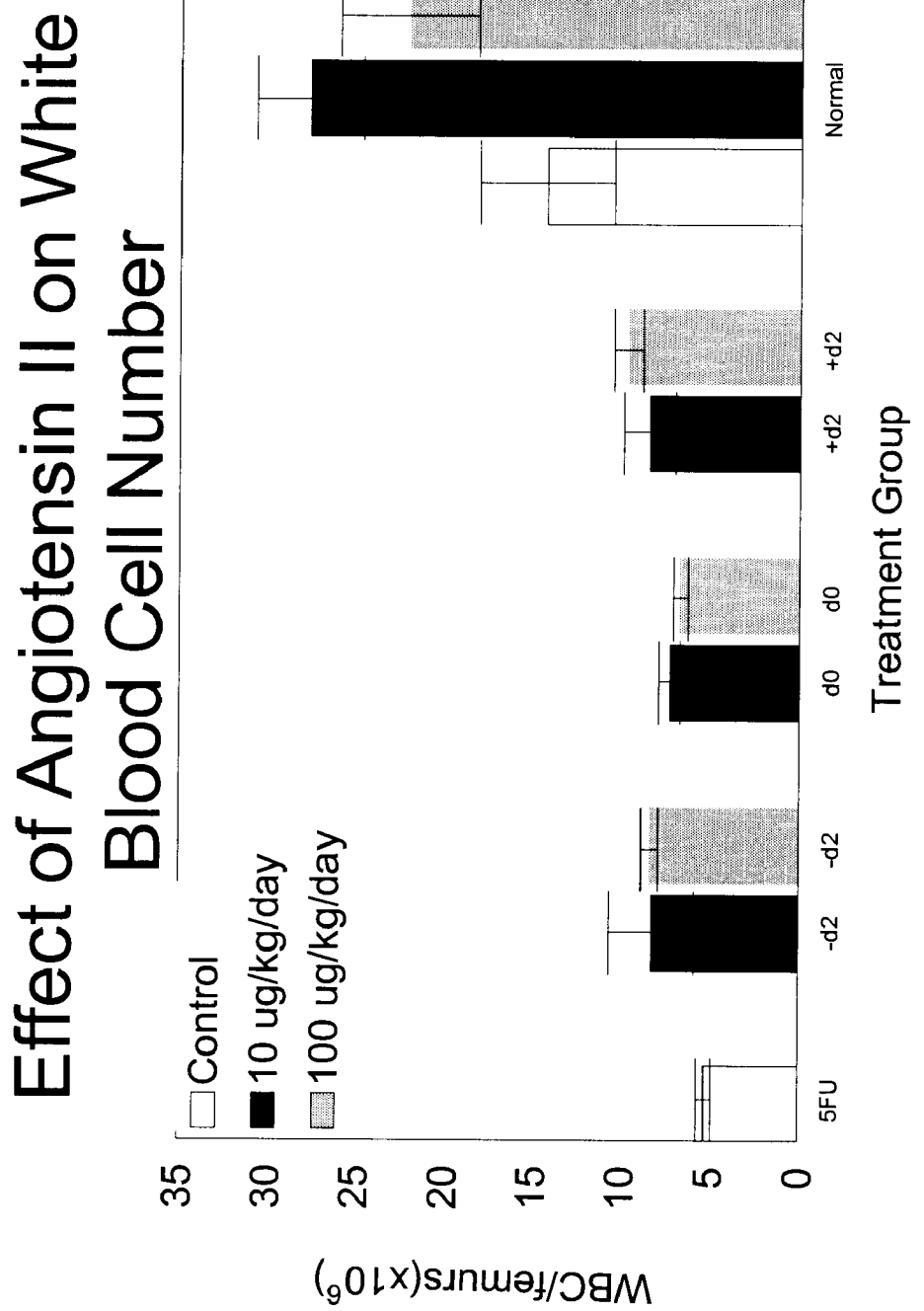
FIG. 4 is a graph showing the effect of AII treatment on white blood cell number in the bone marrow 7 days after 5FU treatment.
Figure 5:
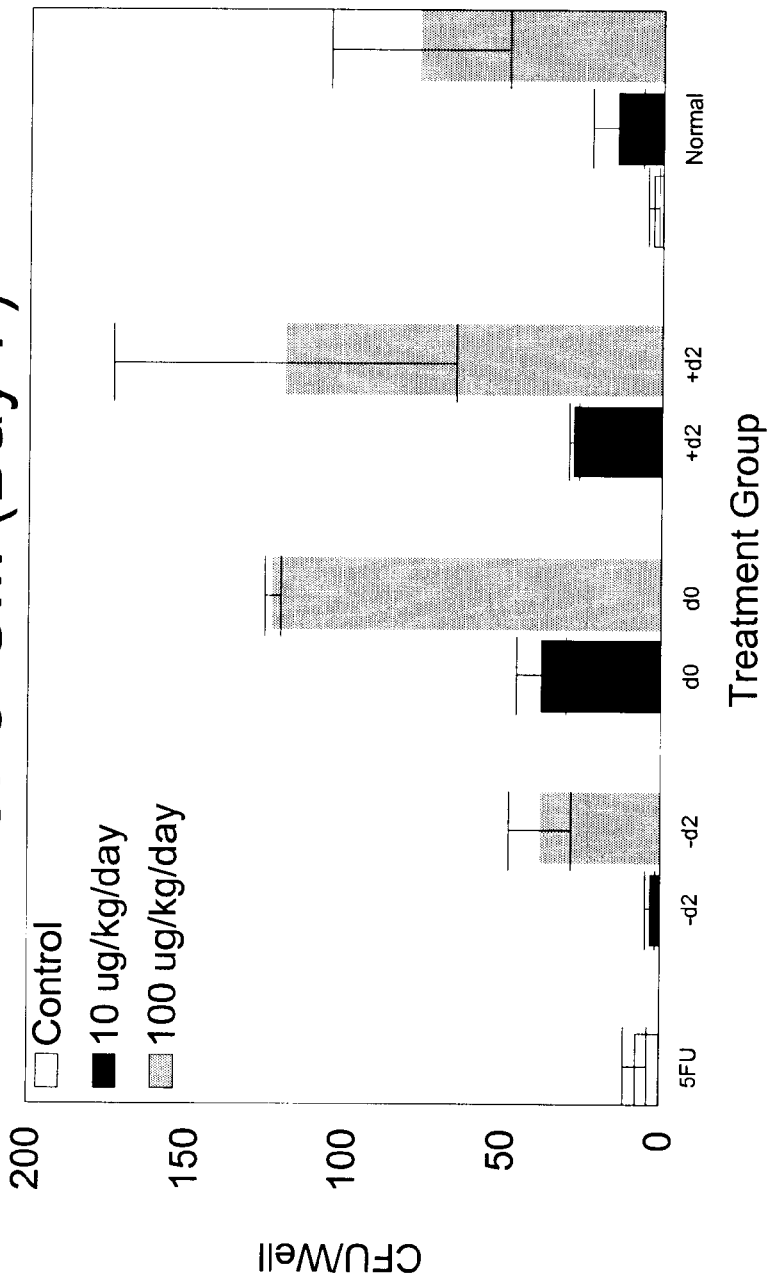
FIG. 5 is a graph showing the effect of AII treatment on CFU-GM cell number on day 7 after culture initiation following blood harvest 7 days after 5FU treatment.
Figure 6:
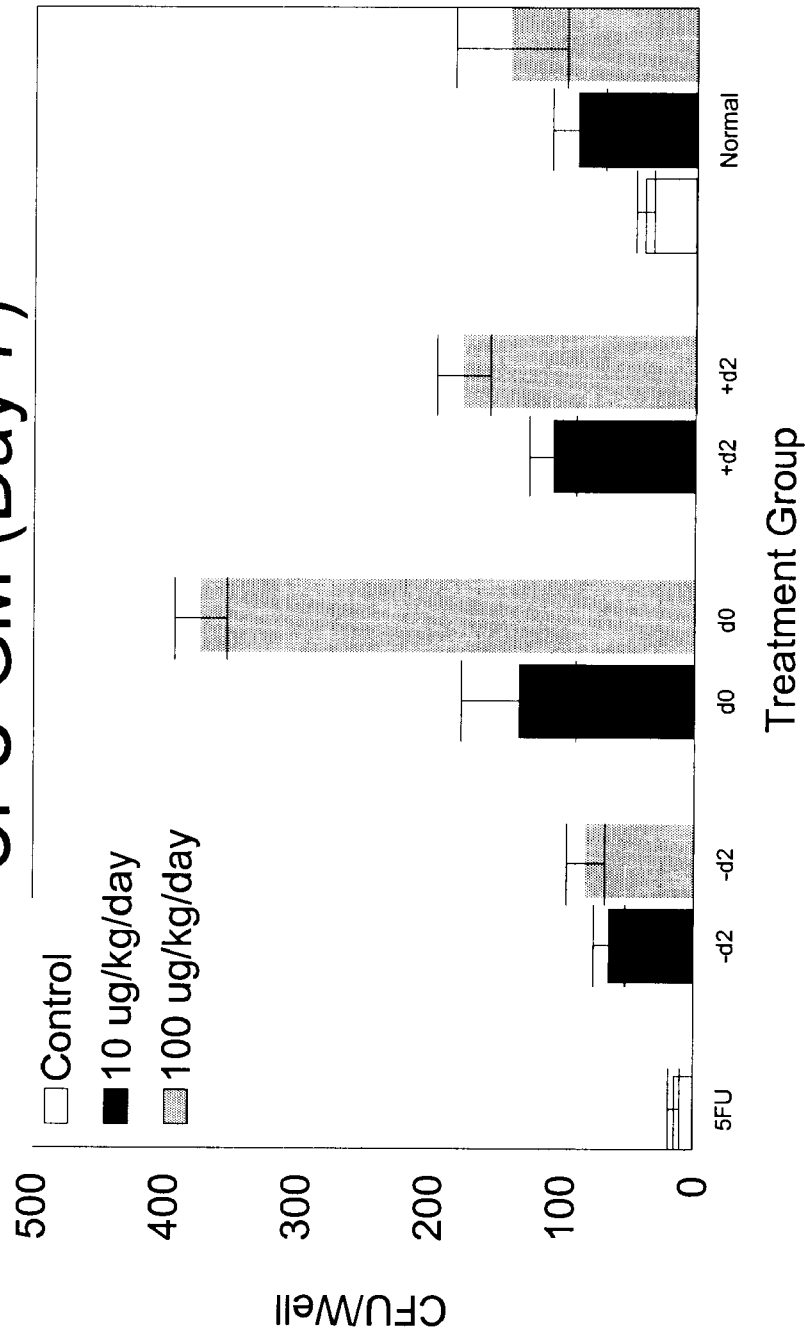
FIG. 6 is a graph showing the effect of AII treatment on CFU-GM cell number on day 7 after culture initiation following spleen harvest 7 days after 5FU treatment.
Figure 7:
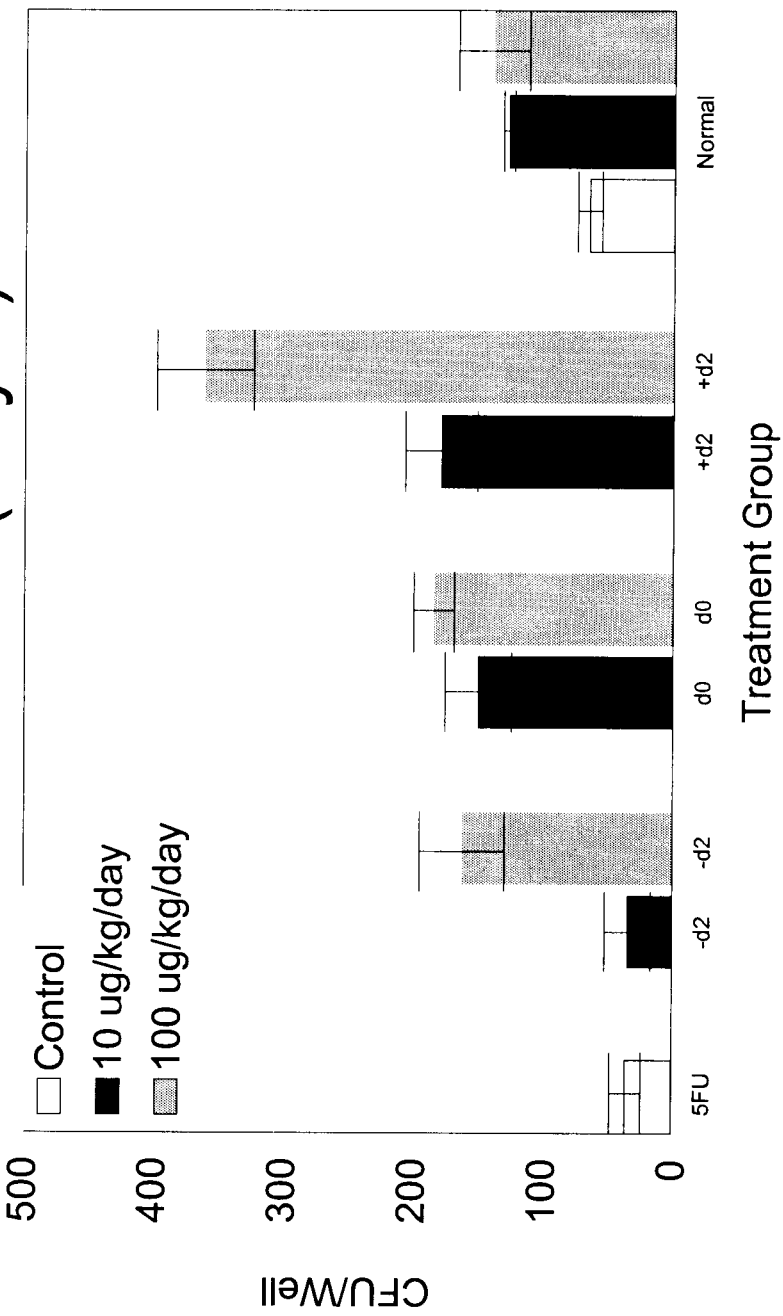
FIG. 7 is a graph showing the effect of AII treatment on CFU-GM cell number on day 7 after culture initiation following bone marrow harvest 7 days after 5FU treatment.
Figure 8:
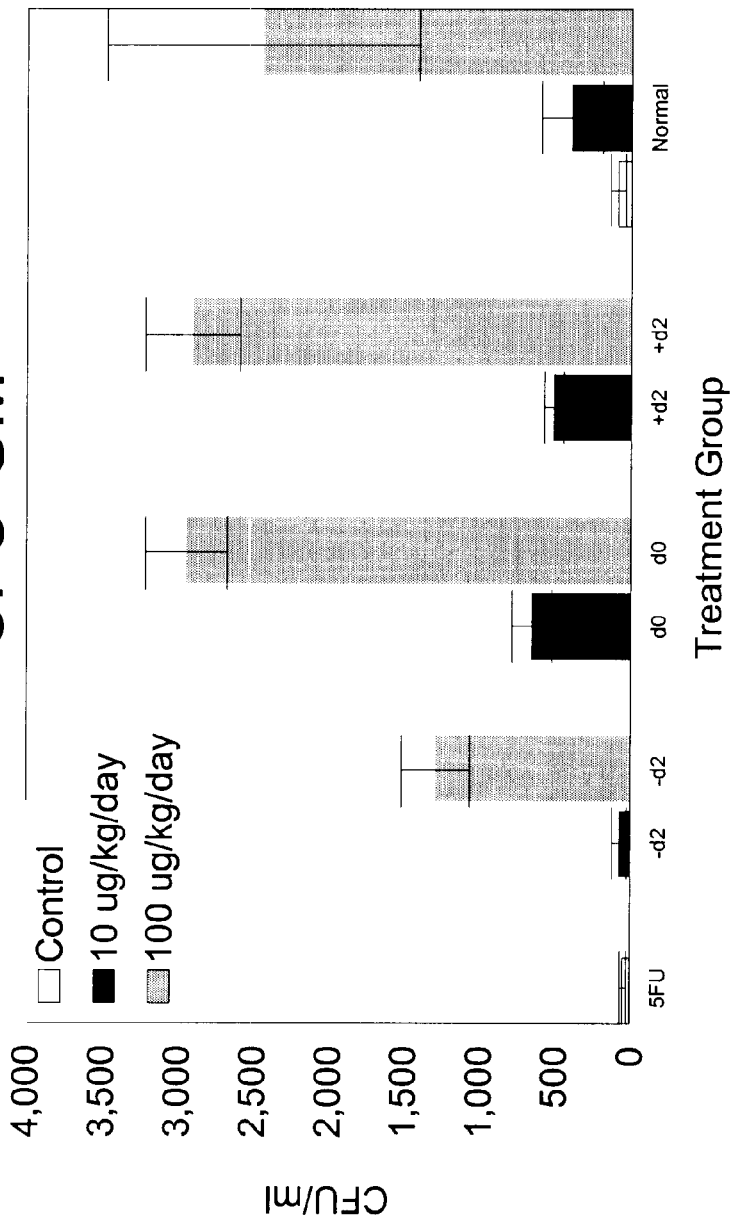
FIG. 8 is a graph showing the effect of AII treatment on CFU-GM cell number in the blood on day 7 after 5FU treatment.
Figure 9:
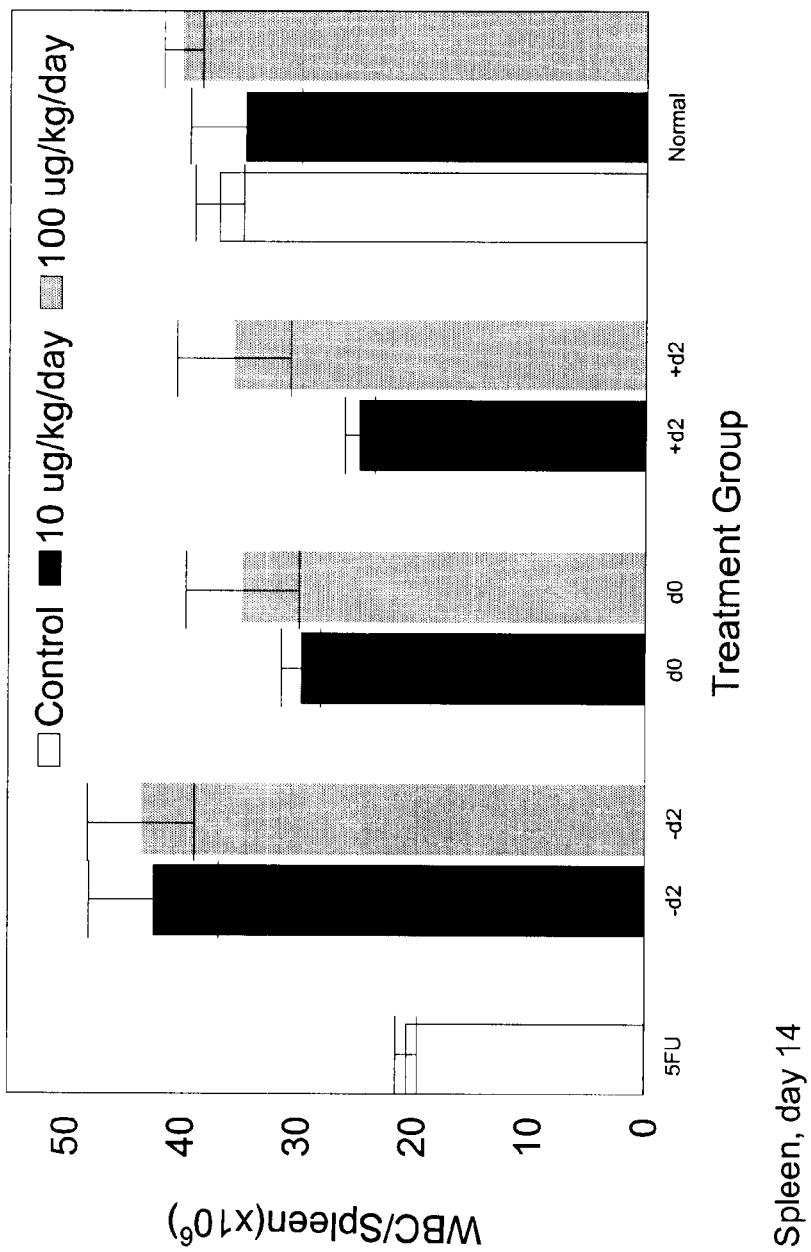
FIG. 9 is a graph showing the effect of AII treatment on white blood cell number in the spleen on day 14 after 5FU treatment.
Figure 10:
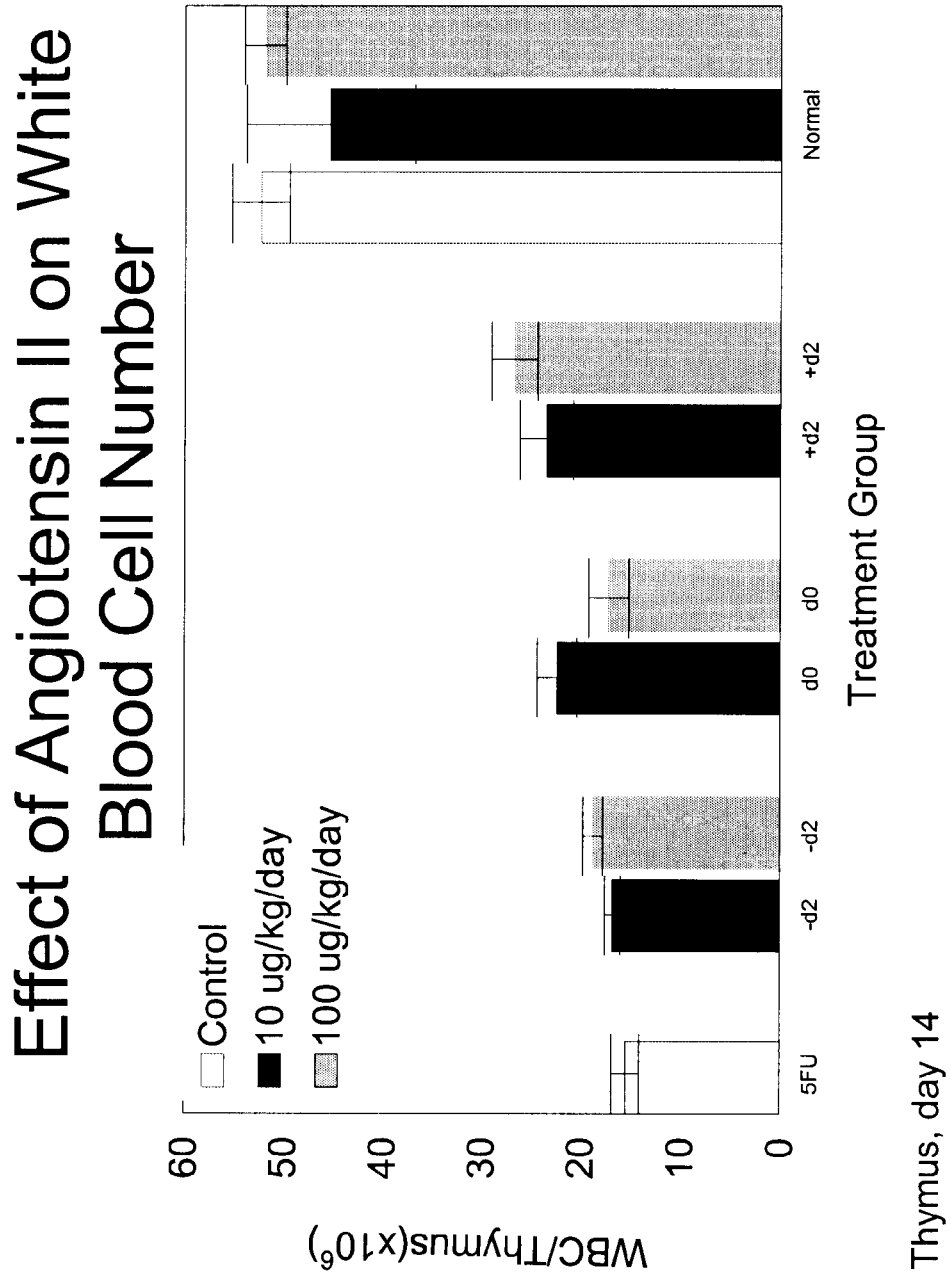
FIG. 10 is a graph showing the effect of AII treatment on white blood cell number in the thymus on day 14 after 5FU treatment.
Figure 11:
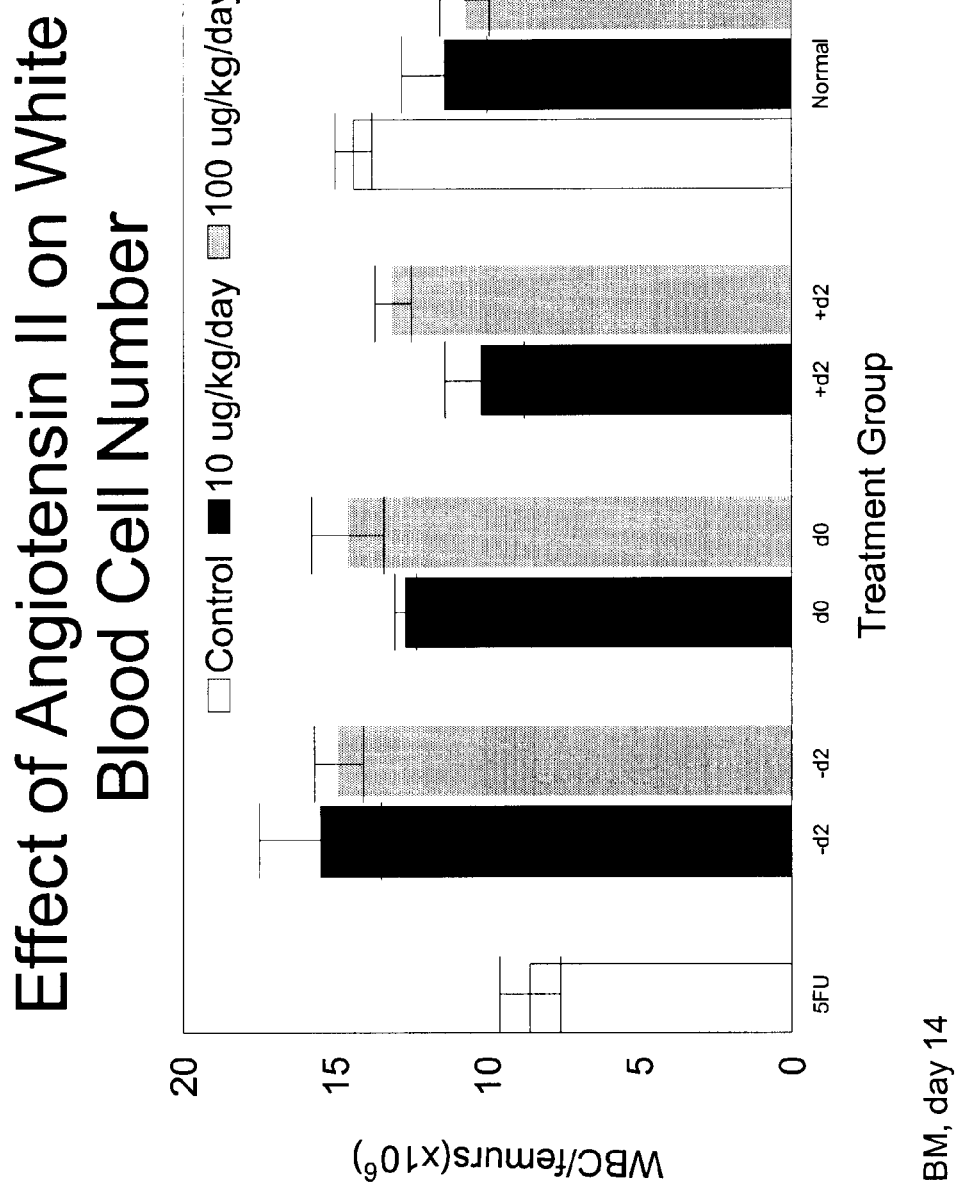
FIG. 11 is a graph showing the effect of AII treatment on white blood cell number in the bone marrow on day 14 after 5FU treatment.
Figure 12:
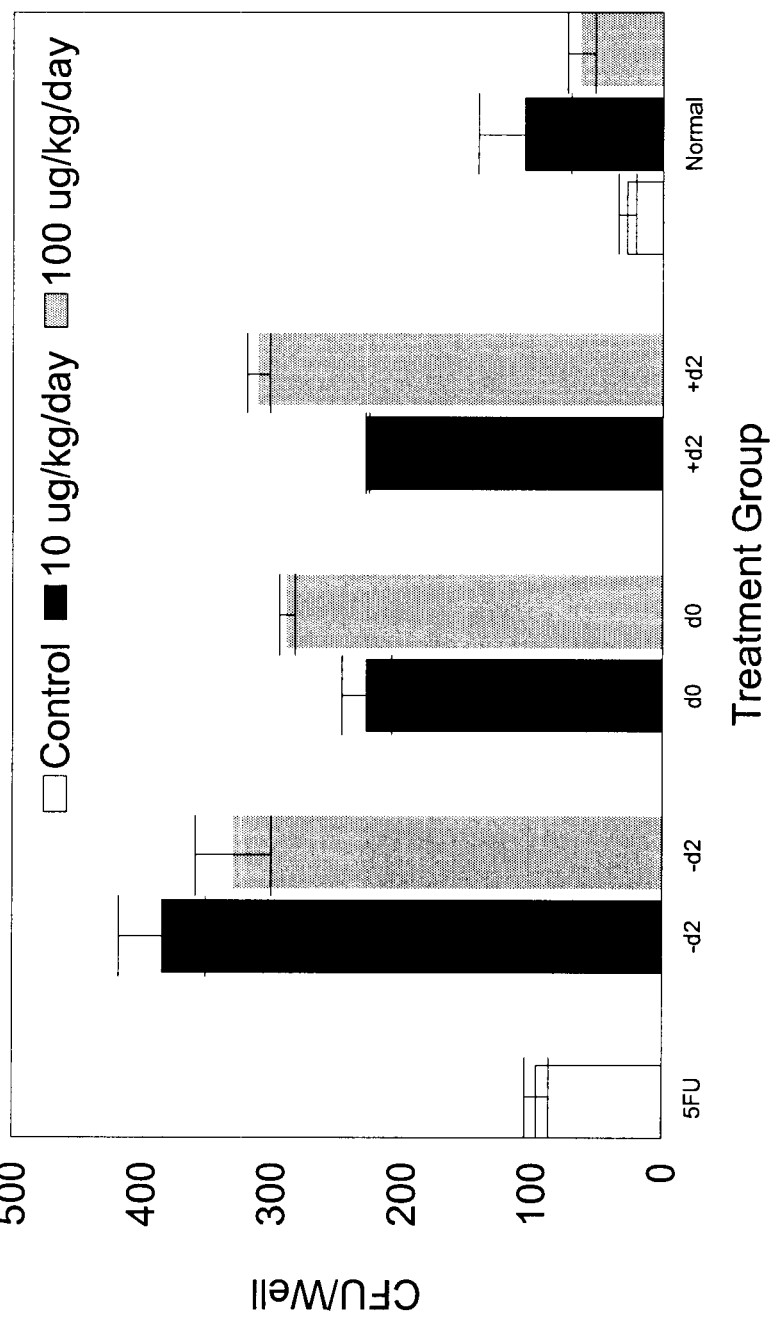
FIG. 12 is a graph showing the effect of AII treatment on CFU-GM cell number on day 7 after culture initiation following spleen harvest 14 days after 5FU treatment.
Figure 13:
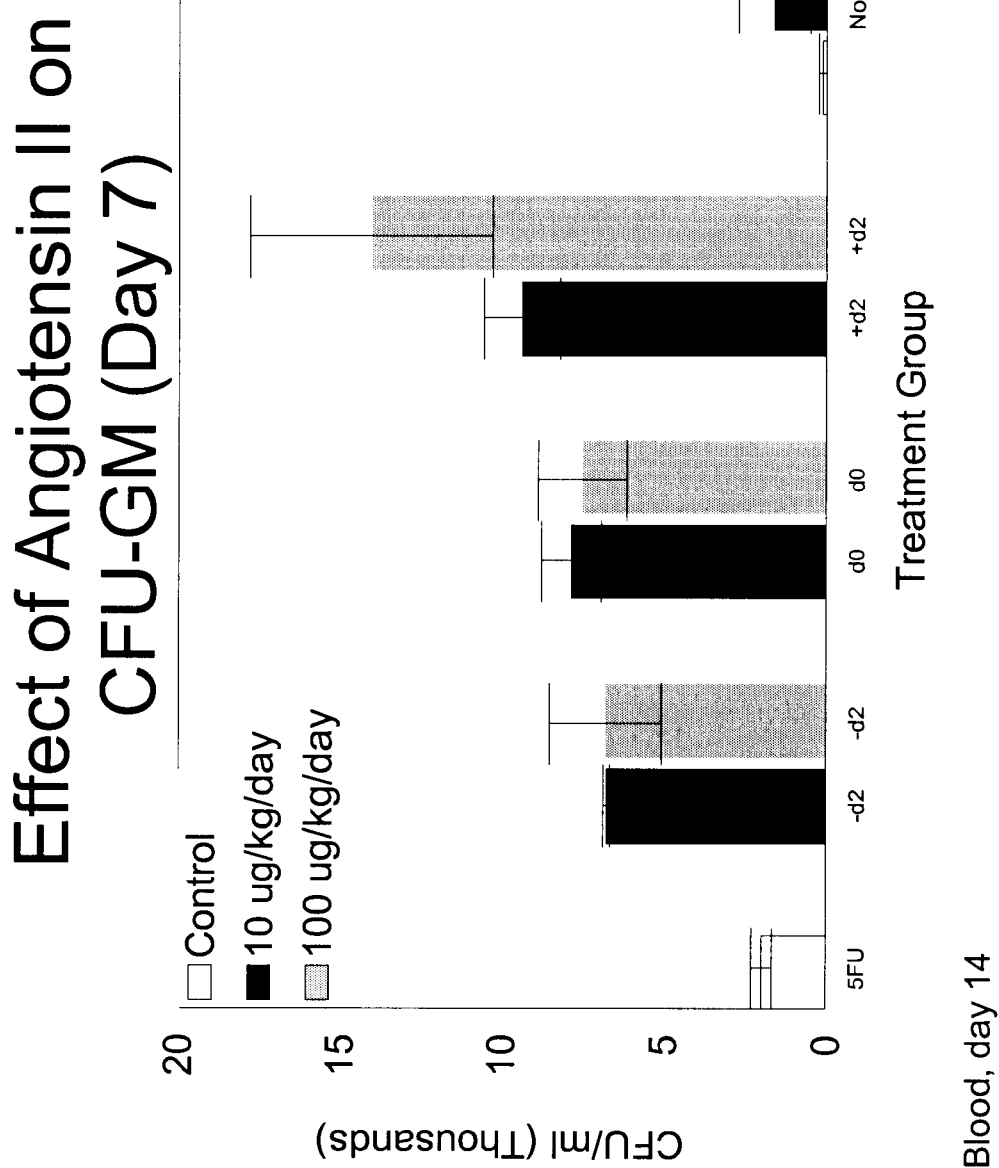
FIG. 13 is a graph showing the effect of AII treatment on CFU-GM cell number on day 7 after culture initiation following blood harvest 14 days after 5FU treatment.
Figure 14:
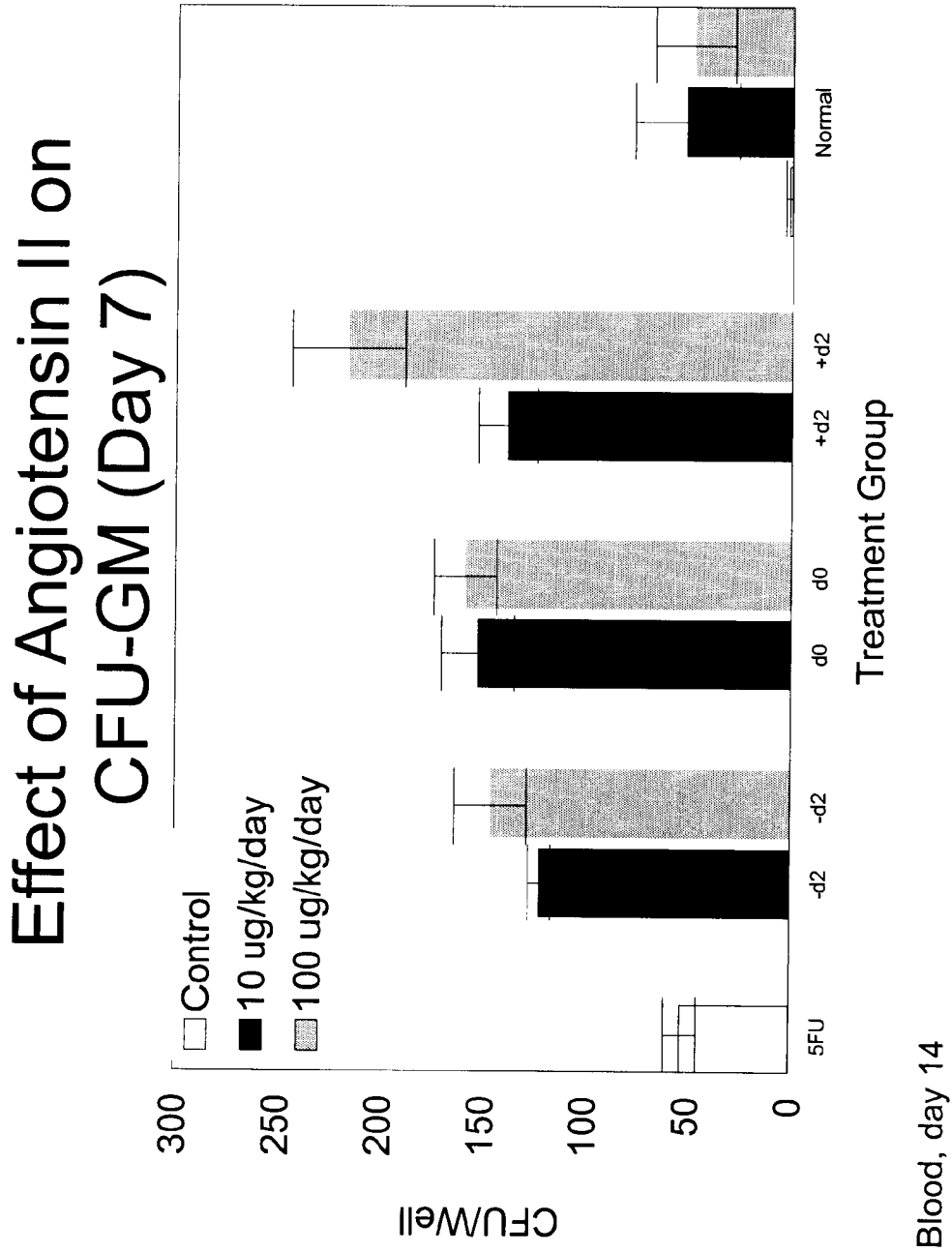
FIG. 14 is a graph showing the effect of AII treatment on CFU-GM cell number on day 7 after culture initiation following blood harvest 14 days after 5FU treatment.
Figure 15:
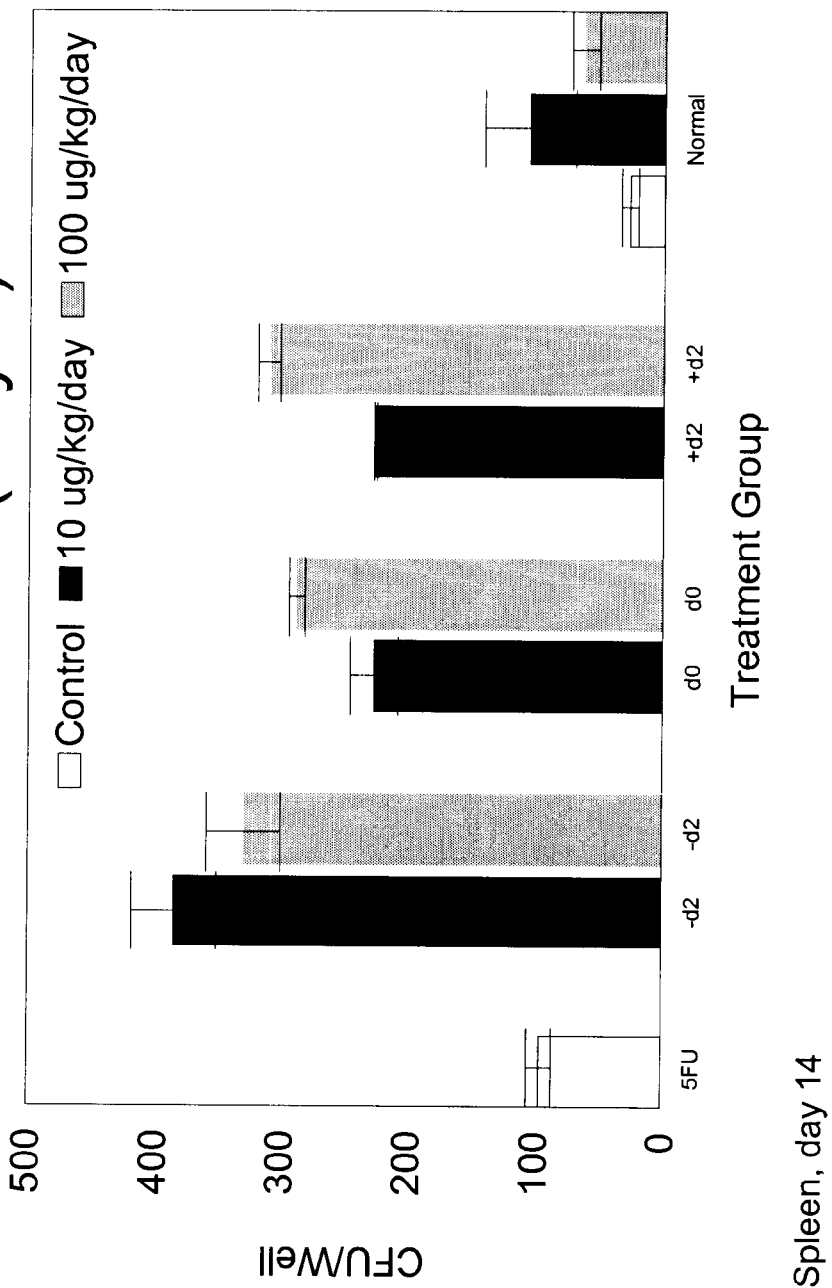
FIG. 15 is a graph showing the effect of AII treatment on CFU-GM cell number on day 7 after culture initiation following spleen harvest 14 days after 5FU treatment.
Figure 16:
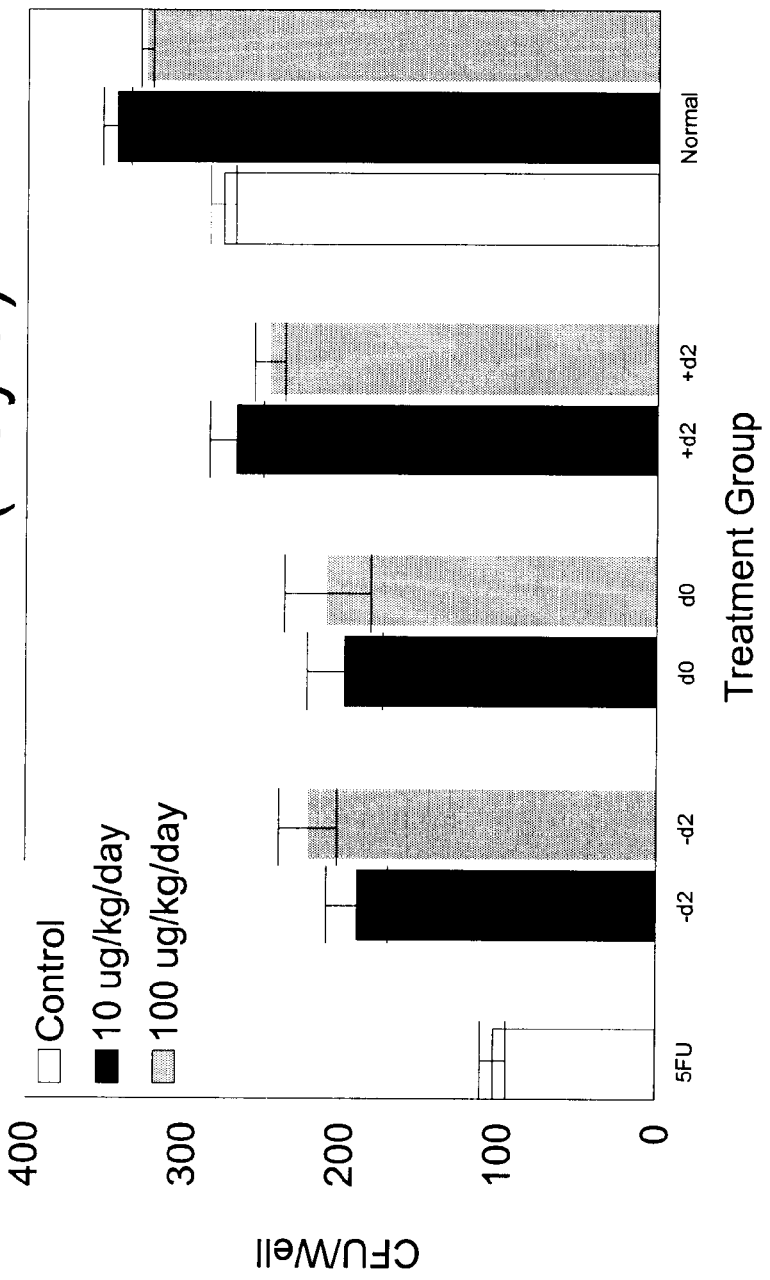
FIG. 16 is a graph showing the effect of AII treatment on CFU-GM cell number on day 7 after culture initiation following bone marrow harvest 7 days after 5FU treatment.
Figure 17:
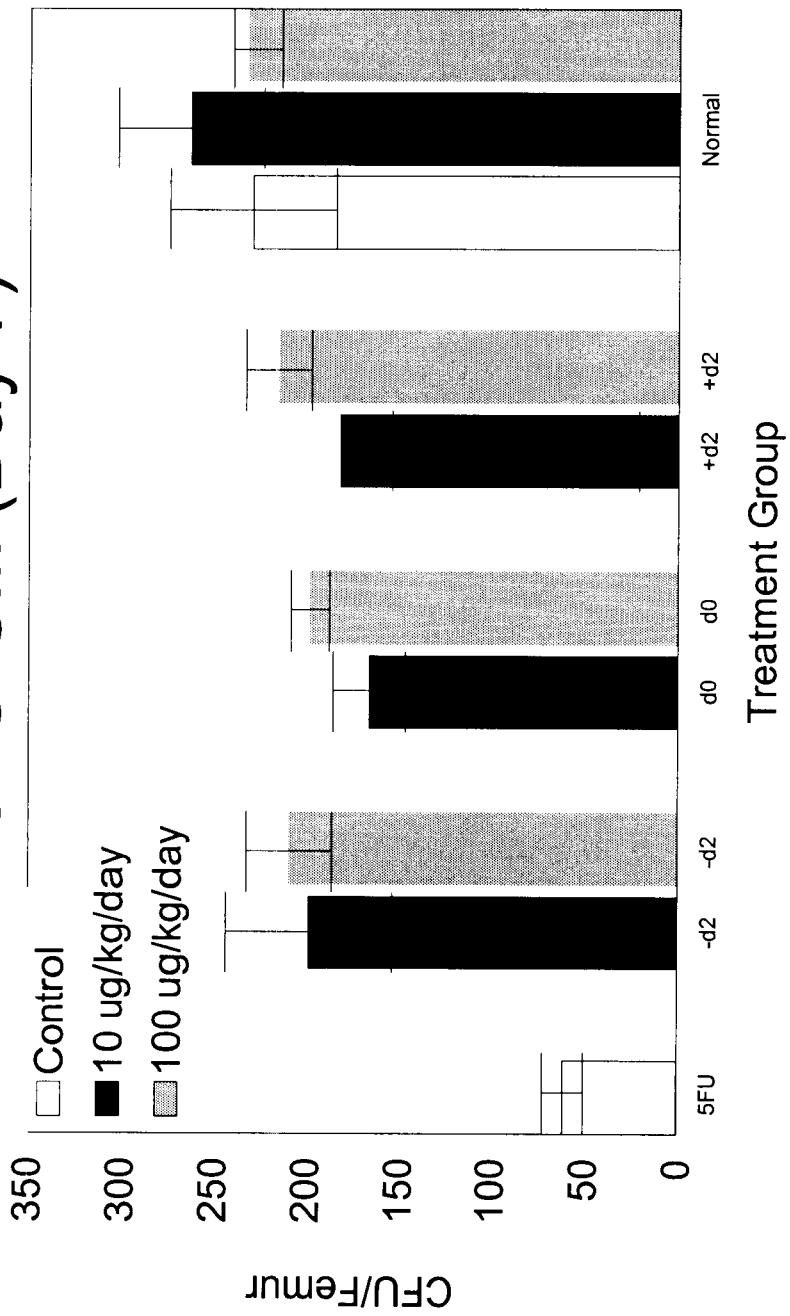
FIG. 17 is a graph showing the effect of AII treatment on CFU-GM cell number on day 7 after culture initiation following femur harvest 7 days after 5FU treatment.
Figure 18:
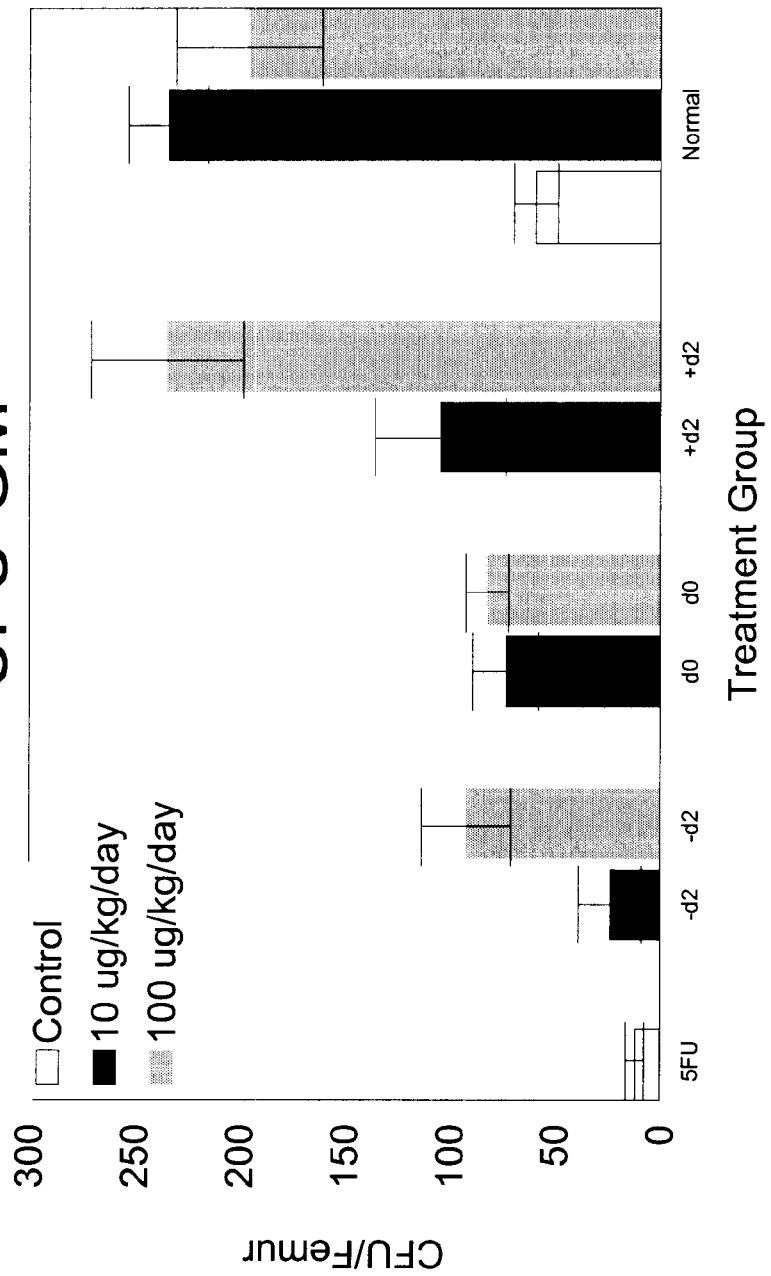
FIG. 18 is a graph showing the effect of AII treatment on CFU-GM cell number in the bone marrow on day 7 after 5FU treatment.
Figure 19:
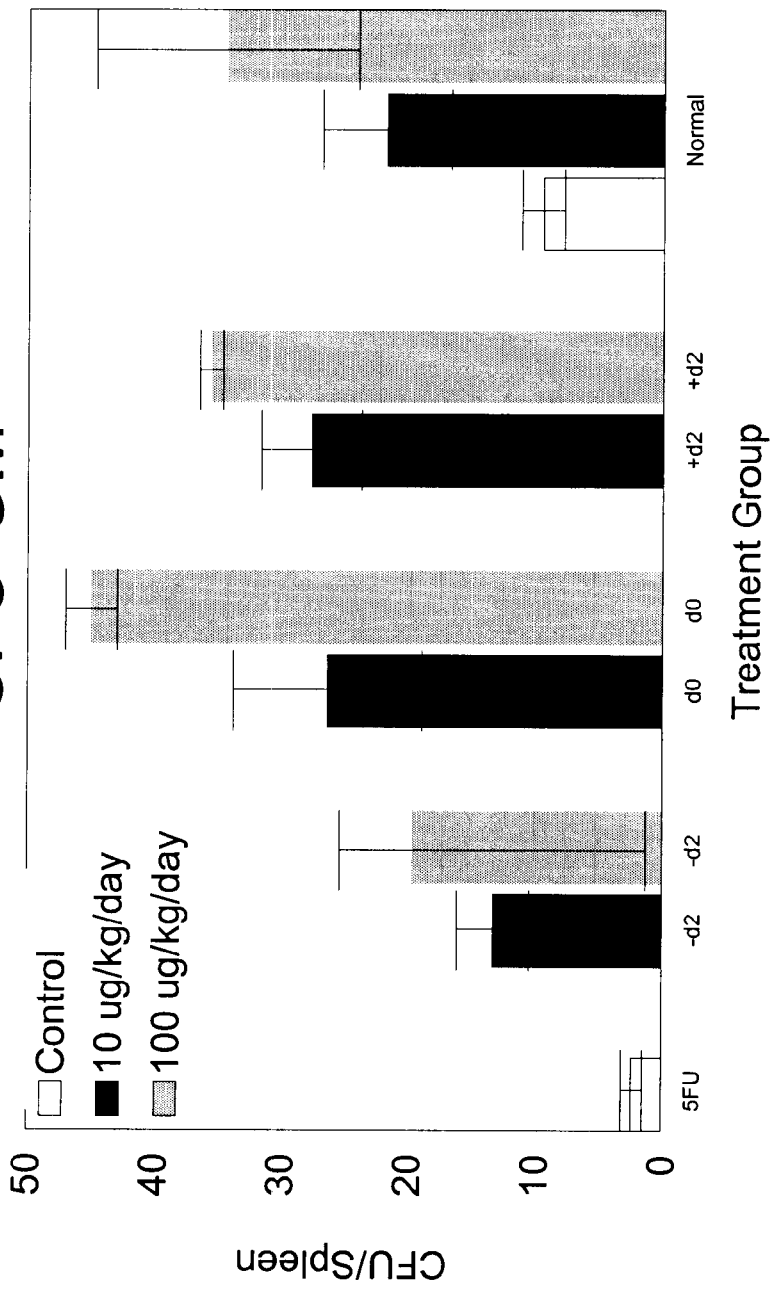
FIG. 19 is a graph showing the effect of AII treatment on CFU-GM cell number in the spleen on day 7 after 5FU treatment.
Figure 20:
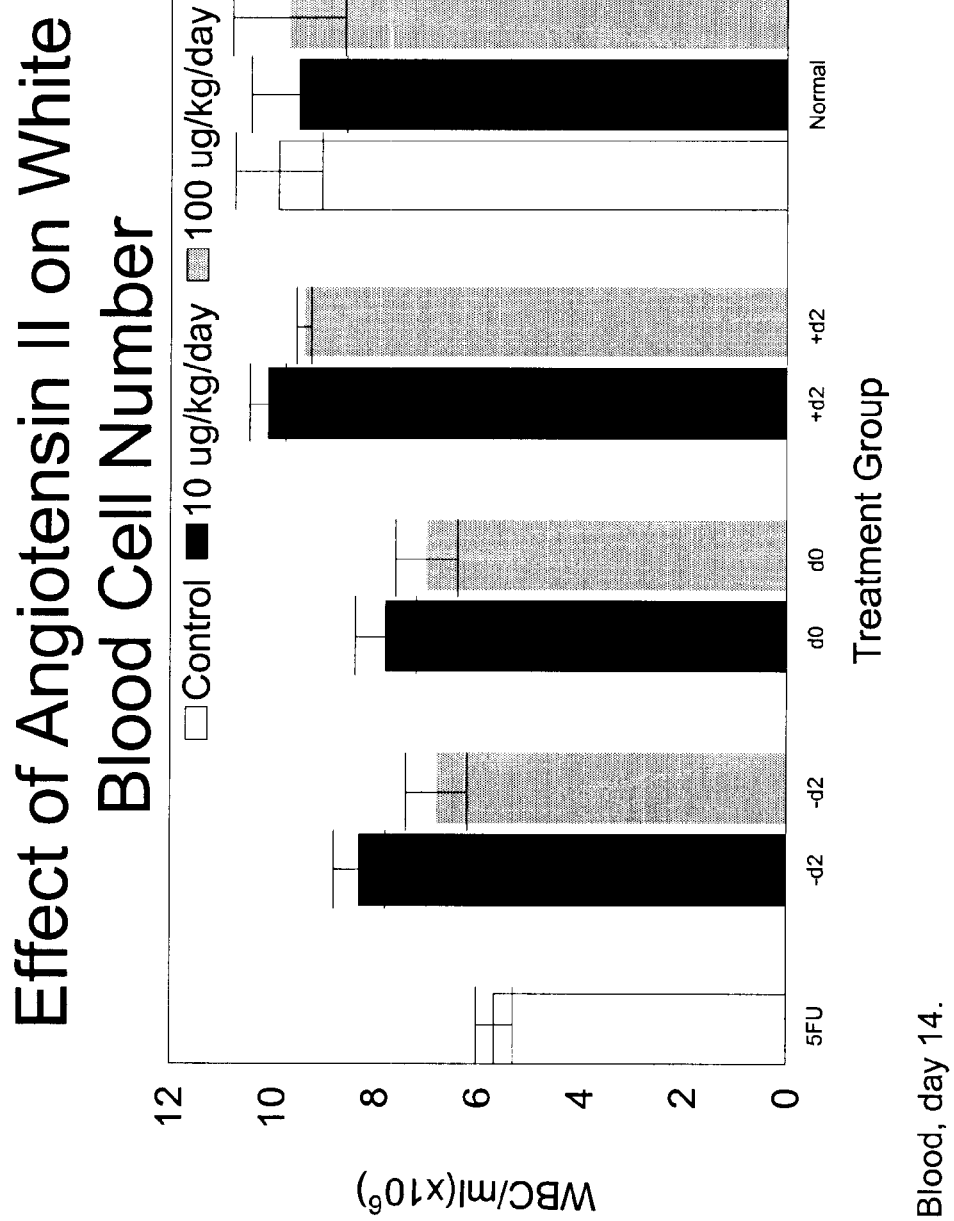
FIG. 20 is a graph showing the effect of AII treatment on white blood cell number in the blood on day 14 after 5FU treatment.

Subcutaneous administration of AII (either 10 or 100 µg/dg/day) was initiated either two days before (−d2), the day of (d0), or two days after (d2) intravenous administration of 5FU. On either day 7 or 14 after 5FU administration, the animals were necropsied and the spleen, thymus, peripheral blood, and bone marrow were harvested. The number of white blood cells in each of the lymphoid organs or the number of CFU-GM present in all the organs except the thymus were then assessed. The number of white blood cells per lymphoid organ was assessed after (1) dissociation of the tissues into a single cell suspension (thymus and spleen), (2) flushing of bone marrow from the femur, or (3) lysis of red blood cells by a hypotonic ammonium chloride solution. An aliquot of the cell suspension was diluted with 0.04% trypan blue and the number of cells was determined by microscopic analysis using a hematocytometer. After counting, the number of cells were adjusted to allow a 1:10 dilution of cells into semi-solid medium containing fetal bovine serum, bovine serum albumin, methyl cellulose, rm stem cell factor, rm interleukin 3, rh interleukin 6, L-glutamine, 2 mercaptoethanol, human transferrin and bovine insulin. On day 7 after culture initiation, the number of CFU-GM per well (and then per organ) was determined by microscopic analysis (FIGS. 1–20). These data demonstrate that AII treatment after chemotherapy leads to significantly enhanced white blood cell mobilization and/or recovery in all of the tissues tested.

EXAMPLE 2

Effect of AII Analogues and Fragments on White Blood Cell Mobilization and Recovery After 5 Fluorouracil Treatment The method was conducted as described above in Example 1, except that mice were injected subcutaneously with 150 mg/kg body weight of 5FU, and AII peptide analogues and fragments were tested. Administration of the peptides (see Table 3) was begun 2 days after and continued until 10 days after 5FU administration, at which time the mice were euthenized for evaluation of bone marrow and blood GM-CFU progenitors. On days 4 and 7 after 5FU administration, blood was taken under anesthesia from the retro-orbital sinus. On day 10, blood was taken by cardiac puncture.

Figure 21:
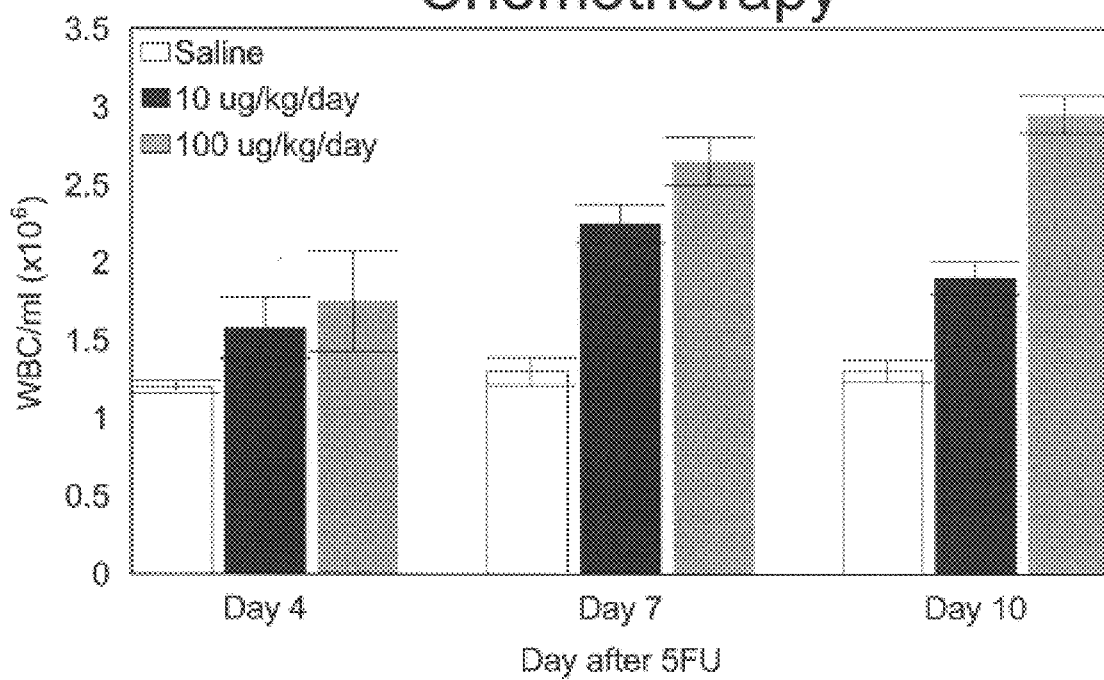
FIG. 21 is a graph of a different experiment showing the effect of AII treatment on white blood cell number in the blood on days 4, 7, and 10 after 5FU treatment.
Figure 22:
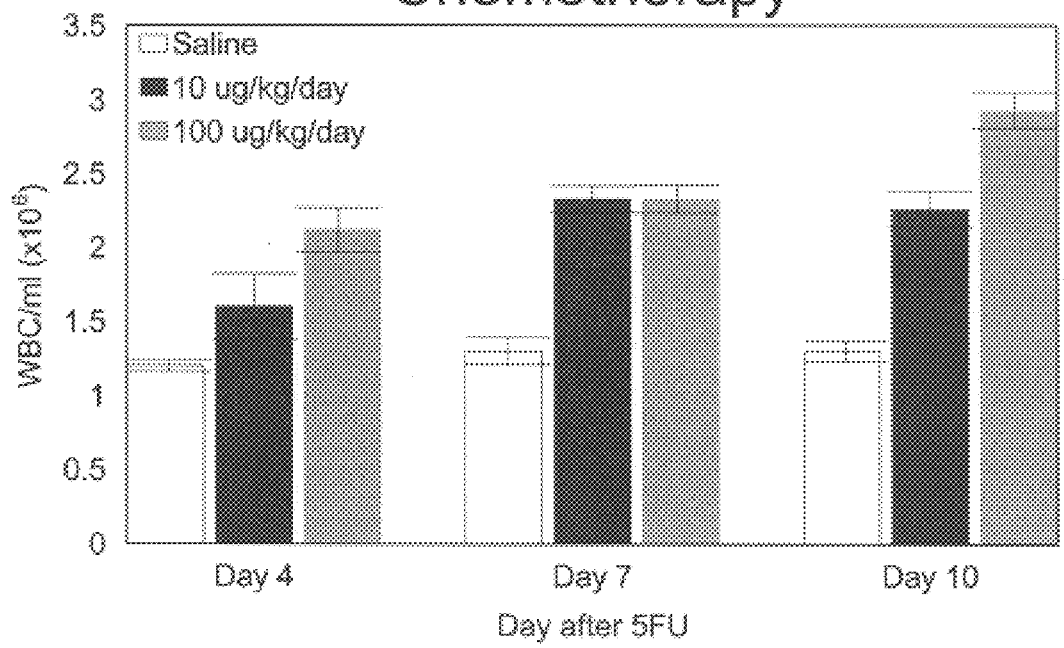
FIG. 22 is a graph showing the effect of AII(1–7) treatment on white blood cell number in the blood on day 14 after 5FU treatment.
Figure 23:
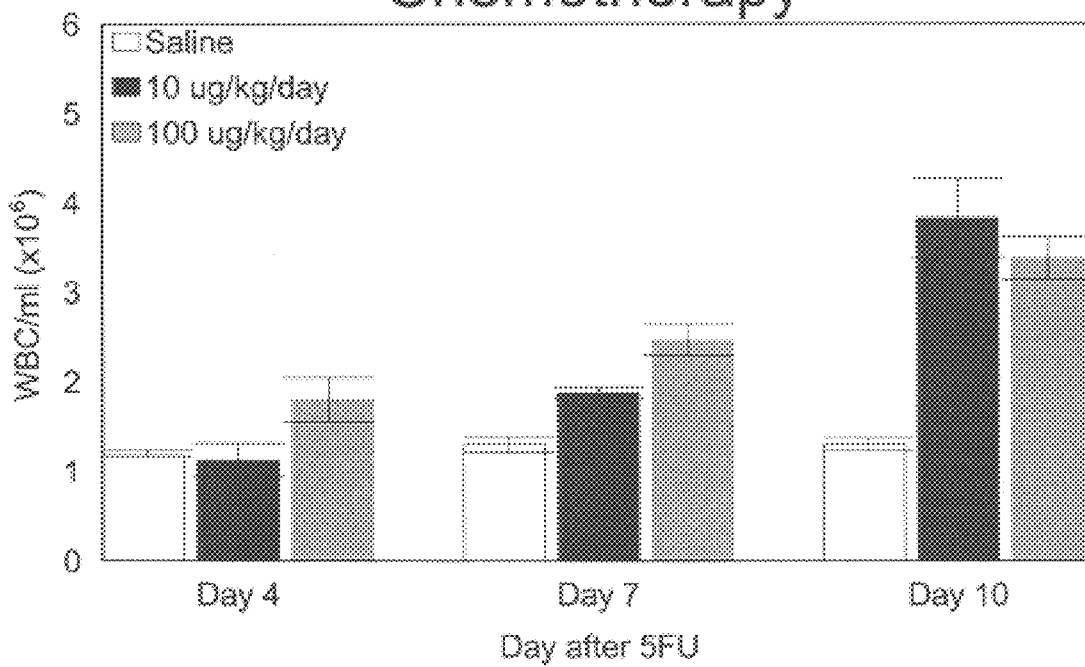
FIG. 23 is a graph showing the effect of 1GD treatment on white blood cell number in the blood on day 14 after 5FU treatment.
Figure 24:
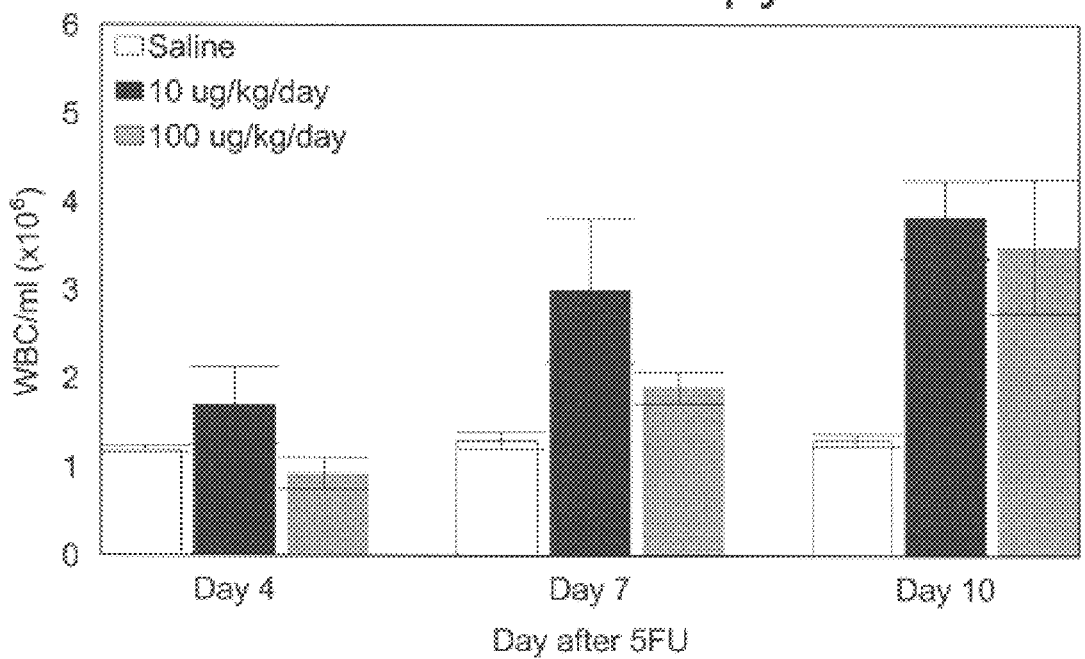
FIG. 24 is a graph showing the effect of 2GD treatment on white blood cell number in the blood on day 14 after 5FU treatment.
Figure 25:
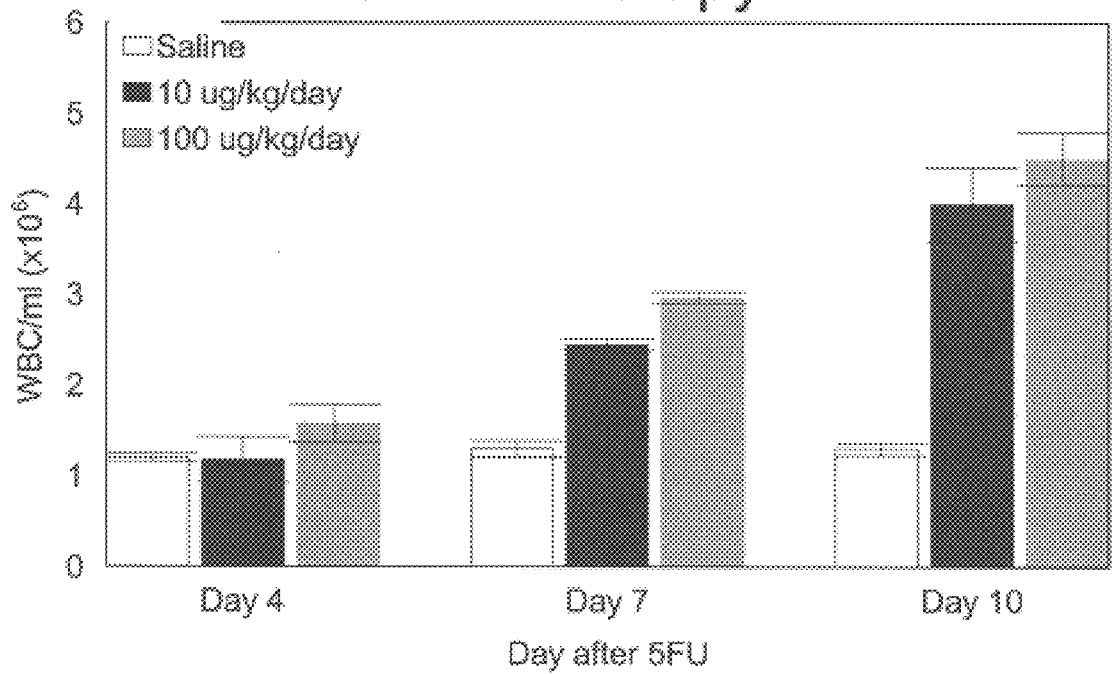
FIG. 25 is a graph showing the effect of 5GD treatment on white blood cell number in the blood on day 14 after 5FU treatment.
Figure 26:
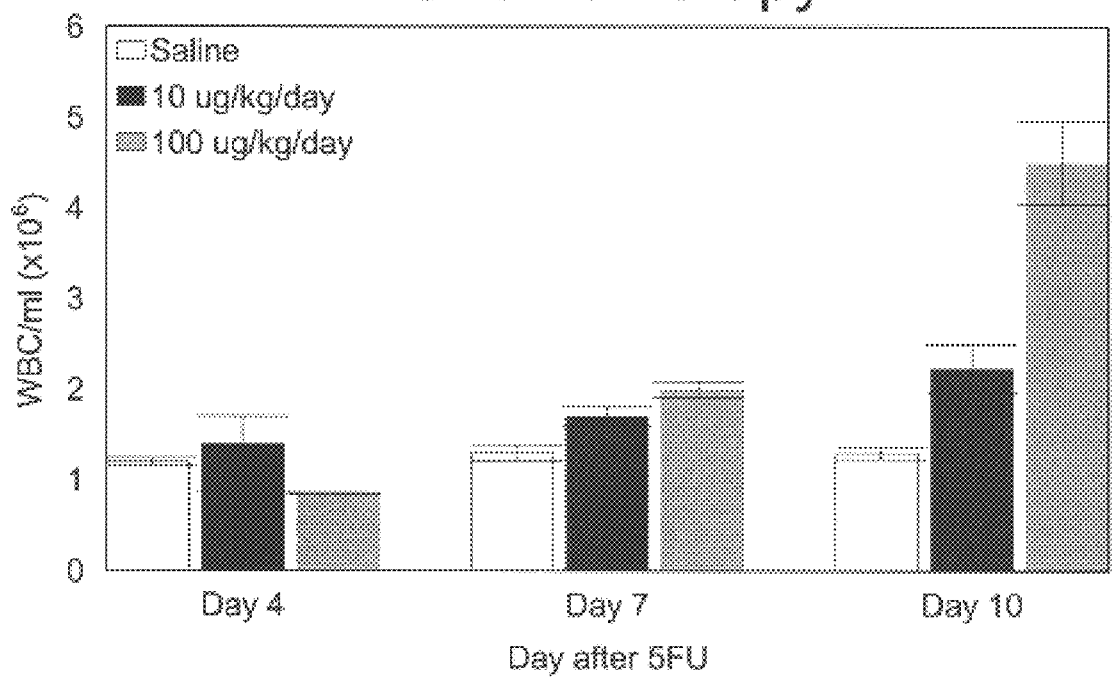
FIG. 26 is a graph showing the effect of 9GD treatment on white blood cell number in the blood on day 14 after 5FU treatment.
Figure 27:
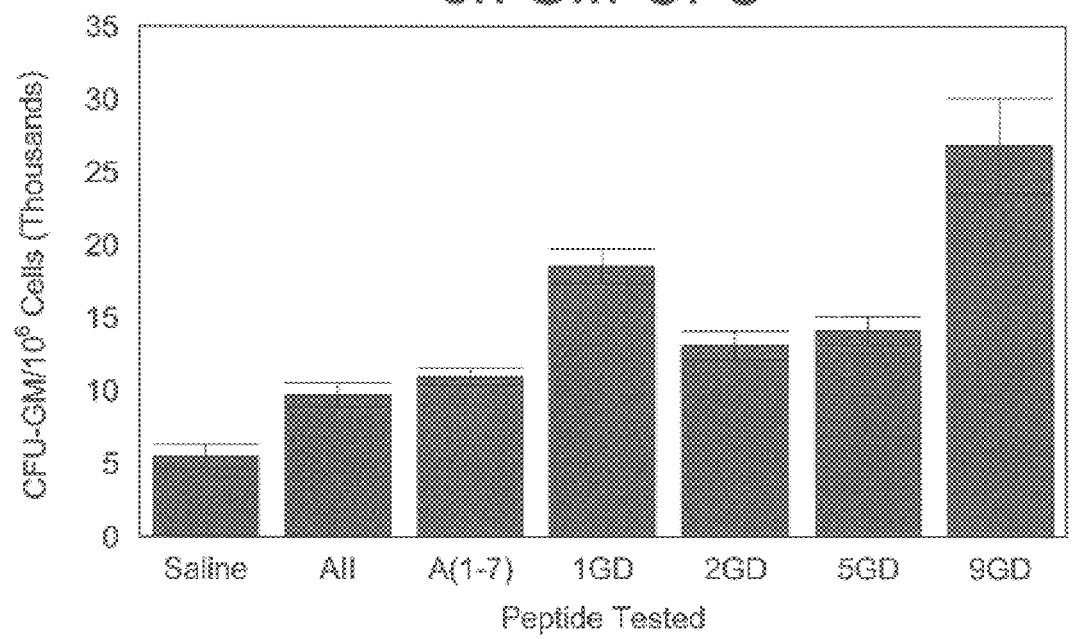
FIG. 27 is a graph showing the effect of 10 μg AII and AII analogues and fragments on GM-CFU numbers in the bone marrow on day 10 after 5FU treatment.
Figure 28:
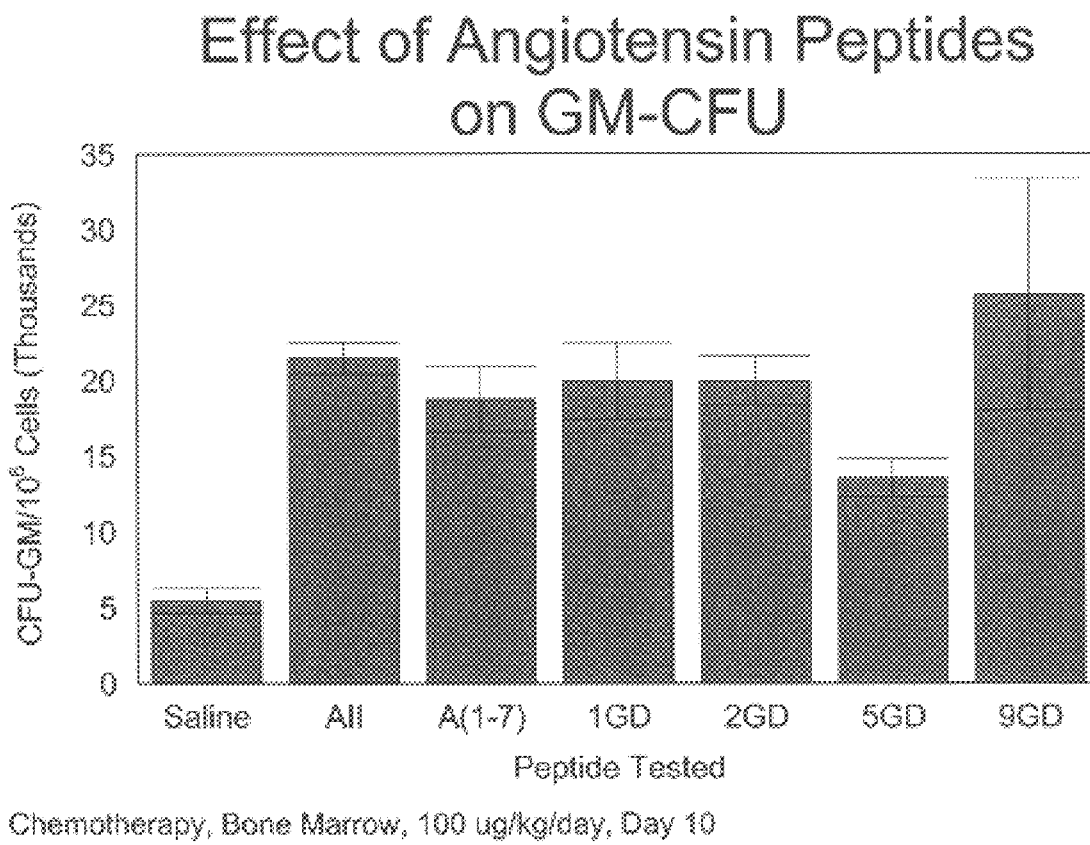
FIG. 28 is a graph showing the effect of 100 [g AII and AII analogues and fragments on GM-CFU numbers in the bone marrow on day 10 after 5FU treatment.
Figure 29:
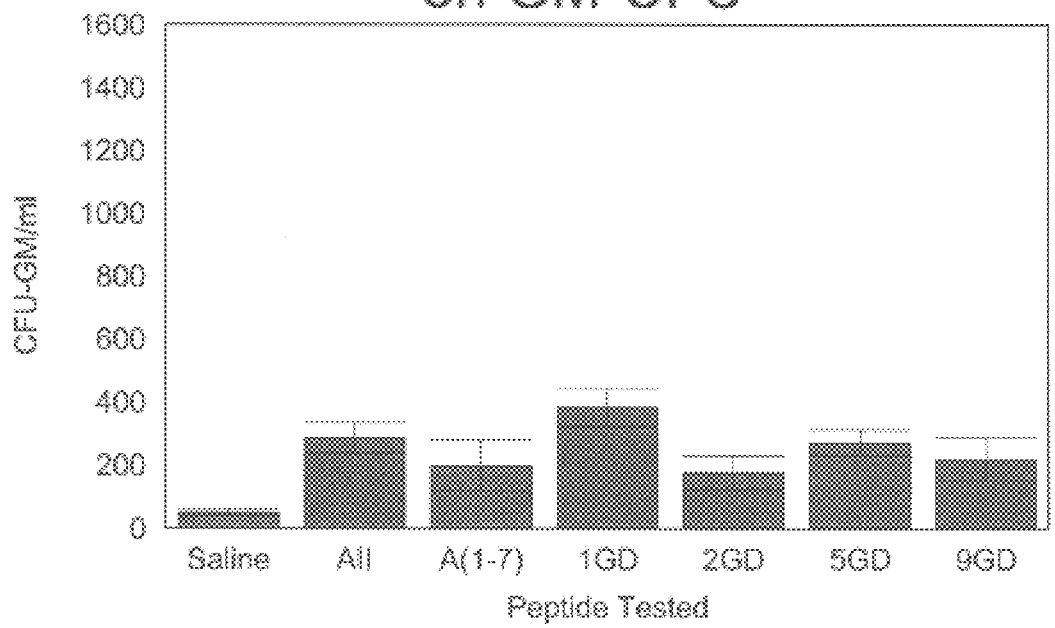
FIG. 29 is a graph showing the effect of 10 μg AII and AII analogues and fragments on GM-CFU numbers in the blood on day 10 after 5FU treatment.
Figure 30:
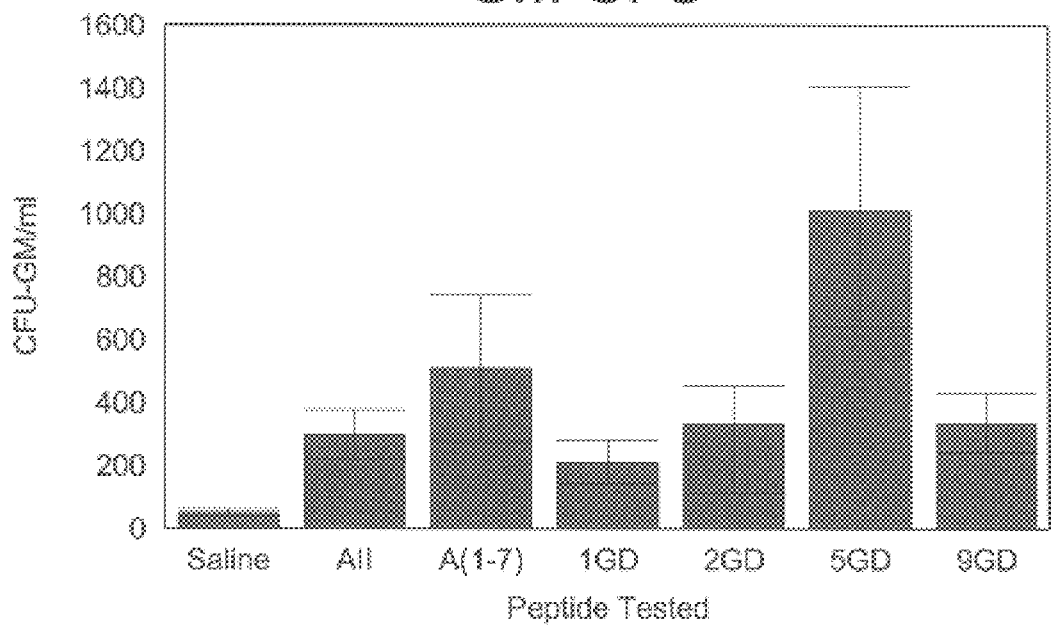
FIG. 30 is a graph showing the effect of 100 μg AII and AII analogues and fragments on GM-CFU numbers in the blood on day 10 after 5FU treatment.

The data for these experiments is shown in FIGS. 21–30, and demonstrate that all peptides tested accelerated the recovery of white blood cells after chemotherapy (FIGS. 21–26), increased the number of GM-CFU progenitors in the bone marrow (FIGS. 27–28), and increased the mobilization of GM-CFU progenitors from the bone marrow into the peripheral blood (FIGS. 29–30), relative to controls. The peptides were effective at both concentrations tested (10 µg/kg/day and 100 µg/kg/day), and the efficacy generally increased with increasing length of treatment.

TABLE 3

Designation for Analogues/Fragments

| Name | Abbreviation | Sequence | SEQ ID NO: |
|---|---|---|---|
| 1GD | Ala4-AII(1-7) | DRVAIHP | SEQ ID NO: 38 |
| 2GD | Pro3-AII(1-7) | DRPYIHP | SEQ ID NO: 39 |
| 5GD | Lys3-MI(1-7) | DRKYIHP | SEQ ID NO: 40 |
| 9GD | NorLeu-AII(1-7) | DR(nor)YIHP | SEQ ID NO: 41 |
| AII(1-7) | | DRVYIHP-- | SEQ ID NO: 4 |
| AII | | DRVYIHPF | SEQ ID NO. 1 |

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the fall scope of the appended claims.

---

We claim:

1. A method for increasing white blood cell survival following chemotherapy comprising the administration of an amount effective for increasing white blood cell survival following chemotherapy of at least one active agent comprising a sequence of the following general formula:

Asp-Arg-R1-R2-Ile-His-Pro-R3 (SEQ ID NO:42), wherein

R1 is selected from the group consisting of Val, Pro, Lys, norLeu, and Leu;

R2 is selected from the group consisting of Ala, Tyr, and Tyr(PO$_3$)$_2$;

R3 is Phe or is absent; and wherein the active agent is not SEQ ID NO:1.

2. The method of claim 1 wherein the active agent is selected from the group consisting of [SEQ ID NO:1,] SEQ ID NO:4, SEQ ID NO:31, SEQ ID NO:32, SEQ ID NO:33, SEQ ID NO:38, SEQ ID NO:39, SEQ ID NO:40, and SEQ ID NO:41.

3. A pharmaceutical composition for use in increasing white blood cell survival and/or mobilizing hematopoietic progenitor cells from bone marrow into peripheral blood following chemotherapy comprising (a) an amount effective for increasing white blood cell survival and/or mobilizing hematopoietic progenitor cells from bone marrow into peripheral blood following chemotherapy of at least one active agent comprising a sequence of the following general formula:

Asp-Arg-R1-R2-Ile-His-Pro-R3 (SEQ ID NO:42), wherein

R1 is selected from the group consisting of Val, Pro, Lys, norLeu, and Leu;

R2 is selected from the group consisting of Ala, Tyr, and Tyr(PO$_3$)$_2$;

R3 is Phe or is absent; and wherein the active agent is not SEQ ID NO:1;

(b) an amount effective for decreasing the growth of tumor cells of a cytotoxic agent; and (c) a pharmaceutically acceptable carrier.

4. The pharmaceutical composition of claim 3 wherein the active agent is selected from the group consisting of SEQ ID NO:4, SEQ ID NO:31, SEQ ID NO:32, SEQ ID NO:33, SEQ ID NO:38, SEQ ID NO:39, SEQ ID NO:40, and SEQ ID NO:41.

5. A method for increasing white blood cell survival following chemotherapy comprising the administration of an amount effective for increasing white blood cell survival following chemotherapy of at least one active agent consisting of a sequence of at least four contiguous amino acids of groups $R^1$–$R^8$ in the sequence of general formula I:

$R^1$-$R^2$-$R^3$-$R^4$-$R^5$-$R^6$$R^7$-$R^8$ wherein $R^1$ is selected from the group consisting of Asp, Glu, Asn, Acpc (1-aminocyclopentane carboxylic acid), Ala, Me$^2$Gly, Pro, Bet, Glu(NH$_2$), Gly, Asp(NH$_2$) and Suc, $R^2$ is selected from the group consisting of Arg, Lys, Ala, Om, Ser(Ac), Sar, D-Arg and D-Lys;

$R^3$ is selected from the group consisting of Val, Ala, Leu, Lys, norLeu, Ile, Gly, Pro, Aib, Acpc, and Tyr;

$R^4$ is selected from the group consisting of Tyr, Tyr (PO$_3$)$_2$, Thr, Ser, Ala, homoSer, and azaTyr;

$R^5$ is selected from the group consisting of Ile, Ala, Leu, norLeu, Val and Gly;

$R^6$ is selected from the group consisting of His, Arg and 6-NH$_2$-Phe;

$R^7$ is selected from the group consisting of Pro and Ala;

$R^8$ is selected from the group consisting of Phe, Phe (Br), Ile and Tyr;

excluding sequences including $R^4$ as a terminal Tyr group; and wherein the active agent is not SEQ ID NO:1.

6. The method of claim 5 wherein the active agent consists of at least five contiguous amino acids of groups $R^1$–$R^8$ in the sequence of general formula I.

7. The method of claim 5 wherein the active agent consists of at least six contiguous amino acids of groups $R^1$–$R^8$ in the sequence of general formula I.

8. The method of claim 5 wherein the active agent consists of at least seven contiguous amino acids of groups $R^1$–$R^8$ in the sequence of general formula I.

9. A method for increasing white blood cell survival following chemotherapy comprising the administration of an amount effective for increasing white blood cell survival following chemotherapy of at least one active agent consisting of a sequence selected from the group consisting of angiotensinogen, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID,NO:32, SEQ ID NO:33, SEQ ID NO:34, SEQ ID NO:35, SEQ ID NO:36, SEQ ID NO:37, SEQ ID NO:38, SEQ ID NO:39, SEQ ID. NO:40, and SEQ ID-NO:41.

10. A method for increasing white blood cell survival following chemotherapy comprising the administration of an amount effective for increasing white blood cell survival following chemotherapy of an active agent comprising the sequence of SEQ ID NO:4, wherein the active agent does not consist of the sequence of SEQ ID NO:1.

11. The method of claim 10 wherein the active agent consists of the sequence of SEQ ID NO:4.

12. A pharmaceutical composition comprising:

(a) an active agent consisting of a sequence of at least four contiguous amino acids of groups $R^1$–$R^8$ in the sequence of general formula I:

$R^1$-$R^2$-$R^3$-$R^4$-$R^5$-$R^6$$R^7$-$R^8$ wherein $R^1$ is selected from the group consisting of Asp, Glu, Asn, Acpc (1-aminocyclopentane carboxylic acid), Ala, Me$^2$Gly, Pro, Bet, Glu(NH$_2$), Gly, Asp(NH$_2$) and Suc, $R^2$ is selected from the group consisting of Arg, Lys, Ala, Om, Ser(Ac), Sar, D-Arg and D-Lys;

$R^3$ is selected from the group consisting of Val, Ala, Leu, Lys, norLeu, Ile, Gly, Pro, Aib, Acpc, and Tyr;

$R^4$ is selected from the group consisting of Tyr, Tyr (PO$_3$)$_2$, Thr, Ser, Ala, homoSer, and azaTyr;

$R^5$ is selected from the group consisting of Ile, Ala, Leu, norLeu, Val and Gly;

$R^6$ is selected from the group consisting of His, Arg and 6-NH$_2$-Phe;

$R^7$ is selected from the group consisting of Pro and Ala;

$R^8$ is selected from the group consisting of Phe, Phe (Br), Ile and Tyr;

excluding sequences including $R^4$ as a terminal Tyr group; and wherein the active agent is not SEQ ID NO: 1;

(b) an amount effective for decreasing the growth of tumor cells of a cytotoxic agent; and (c) a pharmaceutically acceptable carrier.

13. The pharmaceutical composition of claim 12 wherein the active agent consists of a sequence of at least five contiguous amino acids of groups $R^1$–$R^8$ in the sequence of general formula I.

14. The pharmaceutical composition of claim 12 wherein the active agent consists of a sequence of at least six contiguous amino acids of groups $R^1$–$R^8$ in the sequence of general formula I.

15. The pharmaceutical composition of claim 12 wherein the active agent consists of a sequence of at least seven contiguous amino acids of groups $R^1$–$R^8$ in the sequence of general formula I.

16. A pharmaceutical composition comprising (a) an active agent consisting of a sequence selected from the group consisting of angiotensinogen, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO: 16, SEQ ID NO: 17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41;

(b) an amount effective for decreasing the growth of tumor cells of a cytotoxic agent; and (c) a pharmaceutically acceptable carrier.

17. A pharmaceutical composition comprising (a) an active agent comprising the sequence of SEQ ID NO:4, wherein the active agent is not SEQ ID NO:1;

(b) an amount effective for decreasing the growth of tumor cells of a cytotoxic agent; and (c) a pharmaceutically acceptable carrier.

18. The pharmaceutical composition of claim 17 wherein the active agent consists of the sequence of SEQ ID NO:4.

* * * * *

SEQUENCE LISTING

<160> NUMBER OF SEQ ID NOS: 42

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

```
<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
 1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8
```

Asp Arg Val Tyr Ile His
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

Asp Arg Val Tyr
1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<221> NAME/KEY: MOD_RES
<222> LOCATION: (2)
<223> OTHER INFORMATION: Nle

<400> SEQUENCE: 12

Arg Xaa Tyr Ile His Pro Phe
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<221> NAME/KEY: MOD_RES
<222> LOCATION: (4)
<223> OTHER INFORMATION: Nle

<400> SEQUENCE: 13

Arg Val Tyr Xaa His Pro Phe
1               5

<210> SEQ ID NO 14
<211> LENGTH: 3
<212> TYPE: PRT

```
<213> ORGANISM: Artificial Sequence
<220> FEATURE:
<223> OTHER INFORMATION: Description of Artificial Sequence:AII (6-8)

<400> SEQUENCE: 14

His Pro Phe
  1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<221> NAME/KEY: UNSURE
<222> LOCATION: (1)
<223> OTHER INFORMATION: Xaa at poistion 1 can be Arg, Lys, Ala, Orn,
      Ser, MeGly, D-Arg, or D-Lys
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

Arg Val Tyr Ala His Pro Phe
  1               5

<210> SEQ ID NO 19
<211> LENGTH: 8
<212> TYPE: PRT
<213> ORGANISM: Artificial Sequence
```

```
<220> FEATURE:
<223> OTHER INFORMATION: Description of Artificial Sequence:AII analogue
      1

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
 1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue
      3

<400> SEQUENCE: 21

Ala Pro Gly Asp Arg Ile Tyr Val His Pro Phe
 1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII analogue
      6

<400> SEQUENCE: 24

Asp Arg Ala Tyr Ile His Pro Phe
 1               5
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue 7

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue 8

<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue 9

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue 10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue 11

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue 12

```
<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
      14
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<221> NAME/KEY: MOD_RES
<222> LOCATION: (3)
<223> OTHER INFORMATION: Nle

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<221> NAME/KEY: MOD_RES
<222> LOCATION: (5)
<223> OTHER INFORMATION: Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<221> NAME/KEY: MOD_RES
```

```
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial
      Sequence:p-aminophenylalanine 6 AII
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

Asp Arg Val Tyr Ile His Pro Phe His Leu
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:1GD:
      Ala4-AII(1-7)

<400> SEQUENCE: 38

Asp Arg Val Ala Ile His Pro
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:2GD:
      Pro3-AII(1-7)

<400> SEQUENCE: 39

Asp Arg Pro Tyr Ile His Pro
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:5GD:
      Lys3-AII(1-7)

<400> SEQUENCE: 40

Asp Arg Lys Tyr Ile His Pro
```

-continued

```
<210> SEQ ID NO 41
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Nle
<223> OTHER INFORMATION: Description of Artificial Sequence:9GD:
      norLeu-AII(1-7)

<400> SEQUENCE: 41

Asp Arg Xaa Tyr Ile His Pro
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:AII analogue
      class
<221> NAME/KEY: UNSURE
<222> LOCATION: (3)
<223> OTHER INFORMATION: Xaa at poistion 3 can be Val, Pro, Lys, NorLeu,
      or Leu
<221> NAME/KEY: UNSURE
<222> LOCATION: (4)
<223> OTHER INFORMATION: Xaa at position 4 can be Ala, Tyr, or Tyr(PO3)2
<221> NAME/KEY: UNSURE
<222> LOCATION: (8)
<223> OTHER INFORMATION: Xaa at position 8 can be Phe or absent

<400> SEQUENCE: 42

Asp Arg Xaa Xaa Ile His Pro Xaa
 1               5
```